(12) United States Patent
Lemons

(10) Patent No.: US 9,259,006 B2
(45) Date of Patent: Feb. 16, 2016

(54) ANTIMICROBIAL COMPOSITIONS AND METHODS OF USE THEREOF

(75) Inventor: Kel Eugene Lemons, Placerville, CA (US)

(73) Assignee: SmartWash Solutions, LLC, Salinas, CA (US)

( * ) Notice: Subject to any disclaimer, the term of this patent is extended or adjusted under 35 U.S.C. 154(b) by 1266 days.

(21) Appl. No.: 12/243,460

(22) Filed: Oct. 1, 2008

(65) Prior Publication Data

US 2009/0192231 A1 Jul. 30, 2009

Related U.S. Application Data

(60) Provisional application No. 61/024,558, filed on Jan. 30, 2008.

(51) Int. Cl.
| | | |
|---|---|---|
| *A01N 31/02* | (2006.01) | |
| *A01P 1/00* | (2006.01) | |
| *A01N 59/26* | (2006.01) | |
| *A01N 37/02* | (2006.01) | |
| *A01N 37/36* | (2006.01) | |
| *A01N 59/00* | (2006.01) | |
| *A61L 2/18* | (2006.01) | |

(52) U.S. Cl.
CPC ............... *A01N 59/26* (2013.01); *A01N 37/02* (2013.01); *A01N 37/36* (2013.01); *A01N 59/00* (2013.01); *A61L 2/18* (2013.01)

(58) Field of Classification Search
USPC .......................................................... 514/738
See application file for complete search history.

(56) References Cited

U.S. PATENT DOCUMENTS

| | | | |
|---|---|---|---|
| 3,328,294 A | 6/1967 | Self et al. | |
| 3,625,904 A * | 12/1971 | Nosler et al. ................. | 510/377 |
| 3,806,615 A | 4/1974 | Frankenfeld et al. | |
| T964,007 I4 | 11/1977 | Bailey et al. | |
| 4,074,058 A | 2/1978 | Bailey et al. | |
| 4,107,192 A | 8/1978 | Bailey et al. | |
| 4,938,953 A | 7/1990 | Pena | |
| 5,017,612 A | 5/1991 | Nayfa | |
| 5,087,467 A | 2/1992 | Schwank | |
| 5,280,042 A * | 1/1994 | Lopes ............................ | 514/557 |
| 5,362,650 A | 11/1994 | Harp | |
| 5,490,992 A | 2/1996 | Andrews et al. | |
| 5,569,461 A | 10/1996 | Andrews | |
| 5,599,571 A | 2/1997 | Estrada | |
| 5,658,595 A * | 8/1997 | Van Os .................. | A01N 59/00 422/28 |
| 6,045,846 A | 4/2000 | Bautista et al. | |
| 6,080,417 A | 6/2000 | Kramer | |
| 6,086,833 A | 7/2000 | Conners et al. | |
| 6,106,774 A | 8/2000 | Monticello | |
| 6,180,412 B1 | 1/2001 | Kroll | |
| 6,287,617 B1 | 9/2001 | Bender et al. | |
| 6,478,972 B1 | 11/2002 | Shim et al. | |
| 6,533,958 B2 | 3/2003 | Shim et al. | |
| 6,699,907 B1 | 3/2004 | Dee | |
| 6,749,869 B1 | 6/2004 | Richter et al. ................. | 424/665 |
| 7,090,882 B2 | 8/2006 | Koefod et al. | |
| 7,182,966 B2 | 2/2007 | Howarth et al. | |
| 8,043,650 B2 | 10/2011 | Gutzmann et al. | |
| 2002/0094941 A1 | 7/2002 | Schulhoff | |
| 2002/0134317 A1 | 9/2002 | Shane et al. | |
| 2006/0003023 A1 | 1/2006 | Williams | |
| 2006/0269492 A1* | 11/2006 | Narasimhan et al. ........... | 424/62 |
| 2007/0098751 A1 | 5/2007 | Hilgren et al. | |
| 2009/0324789 A1 | 12/2009 | Ho | |

FOREIGN PATENT DOCUMENTS

| | | |
|---|---|---|
| DE | 19850994 A1 | 5/2000 |
| DE | 102005024001 A1 | 11/2006 |
| EP | 0244144 A1 | 11/1987 |
| EP | 0251303 A2 | 1/1988 |
| EP | 0530861 A2 | 3/1993 |
| EP | 0 801 897 A1 | 10/1997 |
| EP | 0801897 A1 | 10/1997 |
| EP | 0953283 A1 | 11/1999 |
| EP | 1685854 A1 | 8/2006 |
| EP | 1876225 A1 | 1/2008 |
| FR | 2851161 A1 | 8/2004 |
| GB | 2319179 A | 5/1998 |
| WO | WO8504107 A1 | 9/1985 |
| WO | WO 89/12469 | 12/1989 |
| WO | WO8912469 A1 | 12/1989 |
| WO | WO9304595 A2 | 3/1993 |
| WO | WO9507616 A1 | 3/1995 |

(Continued)

OTHER PUBLICATIONS

CFNP TAP Review for Propylene Glycol (Oct. 12, 2007).
"Proposed Amendments to the National Lit of Allowed and Prohibited Substances (Livestock)", Jul. 17, 2006, http://www.usda.gov/wps/portal/!ut/p/_s.7_0_A/7_0_1OB?navid=SEARCH&mode=simple&q=national+list+of+allowed+and+prohibited+substances+livestock+karreman&site=usda&x=15&y=11.
Gerald M. Sapers, *Research on Decontamination of Apples by Washing with Detergents and Sanitizing Agents*, Jul. 15-16, 1999.

*Primary Examiner* — Jeffrey S Lundgren
*Assistant Examiner* — Sara E Townsley
(74) *Attorney, Agent, or Firm* — Medlen & Carroll, LLP

(57) ABSTRACT

The invention provides antimicrobial compositions comprising one or more acid and one or more organic diol. In one embodiment, the invention's compositions have an acidic pH. The compositions may optionally further contain one or more oxidizing agent (including stabilized oxidizing agent and/or unstabilized oxidizing agent), and/or one or more surfactant. In particular embodiments, the acid lacks one or both of —NH group and —NH$_2$ group. The invention's compositions are useful in all stages of handling agricultural products, in hospitals, and in commercial and household applications.

26 Claims, 1 Drawing Sheet

(56) References Cited

FOREIGN PATENT DOCUMENTS

| WO | WO9811777 A1 | | 3/1998 |
|----|----|----|----|
| WO | WO99/40792 | * | 8/1999 |
| WO | WO00013656 A1 | | 3/2000 |
| WO | WO0207520 | | 1/2002 |
| WO | WO0008929 A1 | | 2/2002 |
| WO | WO02059244 A2 | | 8/2002 |
| WO | WO2004045281 A2 | | 6/2004 |
| WO | WO2005070205 A1 | | 8/2005 |
| WO | WO 2006/062847 A2 | | 6/2006 |
| WO | WO 2007/018907 | | 2/2007 |
| WO | WO2009037231 A1 | | 3/2009 |

* cited by examiner

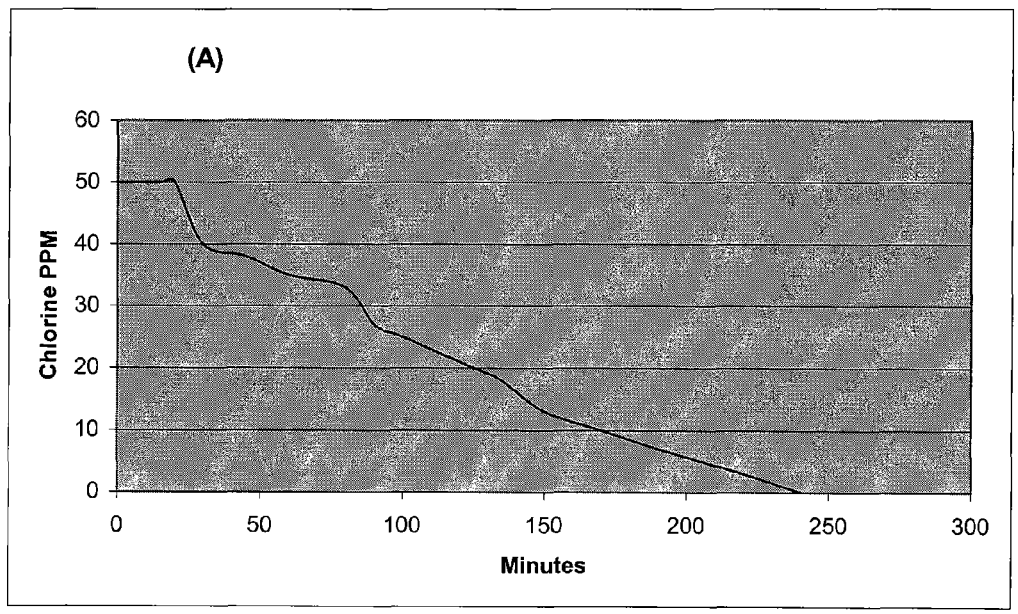
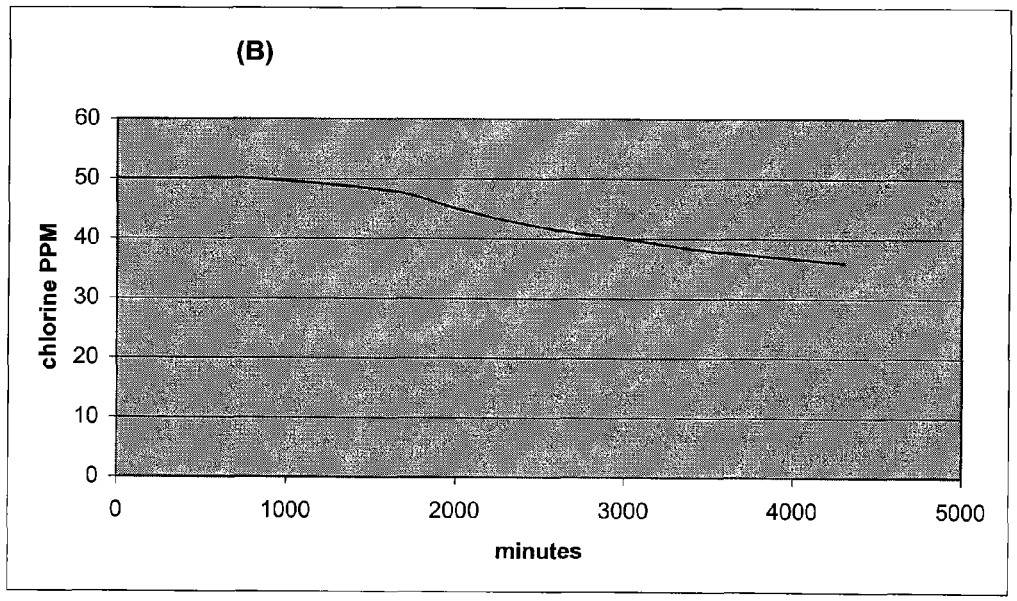

ANTIMICROBIAL COMPOSITIONS AND METHODS OF USE THEREOF

This application claims priority under 35 U.S.C. §119(e) to U.S. Provisional Application Ser. No. 61/024,558 to Kel Eugene Lemons, filed Jan. 30, 2008, herein incorporated by reference in its entirety for all purposes.

FIELD OF THE INVENTION

The invention provides antimicrobial compositions comprising one or more acid and one or more organic diol. In one embodiment, the invention's compositions have an acidic pH. The compositions may optionally further contain one or more oxidizing agent (including stabilized oxidizing agent and/or unstabilized oxidizing agent), and/or one or more surfactant. In particular embodiments, the acid lacks one or both of —NH group and —NH$_2$ group. The invention's compositions are useful in all stages of preparation of agricultural products, in hospitals, and in commercial and household applications.

BACKGROUND OF THE INVENTION

Microbial contamination of food, in hospitals, in animals, as well as in commercial and residential buildings continues to be a problem. In particular, pathogenic microbial contamination of fruits and vegetables has been on the rise, including contamination of fruits and vegetables in the field, during harvesting, transport and/or processing, by pathogenic microbes from animals, humans, organic fertilizer and/or water supply. Bacteria are estimated to cause some 24 million cases of diarrheal disease annually in the U.S. Over 40,000 cases of contamination by *Salmonella* were reported from 1983 to 1987 in laboratory surveillance data.

Several compositions and methods are available for reducing microbial contamination (e.g., Bailey et al., U.S. Pat. No. T964,007 and U.S. Pat. No. 4,074,058; Faergemann et al., WO/89/12469; Andrews et al., U.S. Pat. No. 5,490,992; Estrada, U.S. Pat. No. 5,599,571; Andrews, U.S. Pat. No. 5,569,461; Bautista et al., U.S. Pat. No. 6,045,846; Conners et al., U.S. Pat. No. 6,086,833; Bender et al., U.S. Pat. No. 6,287,617; Koefod et al., U.S. Pat. No. 7,090,882 Howarth et al., U.S. Pat. No. 7,182,966; Shane et al., U.S. Patent Application US 2002/0134317; and Hilgren et al., U.S. Patent Application US 2007/0098751), including those that contain oxidizers. However, prior art compositions that contain oxidizers continue to show low antimicrobial activity in the presence of organic contaminants, and especially at the lower temperatures used for processing, storing and transporting agricultural products. Also, the prior art's compositions have the additional problems of increased foaming and of the oxidizer gassing out of the solution due to bio-load and/or too low or too high pH, thus adversely impacting active ingredients and worker safety. Furthermore, higher levels of oxidizers are required to reduce bio-load and turbidity of the solutions used for antimicrobial treatment, which raises safety concerns when ingesting products that are treated with those compositions. In addition, the presence of plant material in the prior art solutions reduces the longevity of the oxidizer, thus reducing its antimicrobial activity and increasing the cost of production because of the need to replenish the oxidizer often.

Thus, there remains a need for improved compositions and methods for reducing microbial contamination.

SUMMARY OF THE INVENTION

The invention provides an aqueous composition comprising an (a) acid that does not contain an —NH group and an —NH$_2$ group, and (b) organic diol, wherein the composition (i) has acidic pH and (ii) has antimicrobial activity. In a particular embodiment, the amount of the acid alone and the organic diol alone has lower antimicrobial activity compared to antimicrobial activity of a combination of the acid and the organic diol.

While not intending to limit the type of acid in any of the invention's compositions, in one embodiment, the acid comprises an organic acid, as exemplified by, but not limited to, citric acid, ascorbic acid, lactic acid, malic acid, octenic acid, oxalic acid, ursolic acid, hydroxyethanoic acid and salts of each of the organic acid. In another embodiment, the acid comprises an inorganic acid as exemplified by, but not limited to, ortho-phosphoric acid, chromic acid, hydrobromic acid, hydrochloric acid, nitric acid, sulfuric acid, and salts of each of the inorganic acid. In yet a further embodiment, the acid is exemplified by, but not limited to, acetic acid, adipic acid, benzoic acid, glutaric acid, isoascorbic acid, lactic acid, mandelic acid, phosphoric acid, propionic acid, salicylic acid, sorbic acid, succinic acid, tartaric acid, sodium acid pyrophosphate, acidic sodium hexametaphosphate, ethylenediaminetetraacetic acid and salts of each of the acid. Without intending to limit the amount of the acid in any of the invention's compositions, in one embodiment, the composition comprises from 0.001 wgt. % to 40 wgt. % of the acid. In one embodiment, at least one acid in the composition is generally recognized as safe (GRAS).

It is not intended that the type and/or amount of organic diol in any of the invention's compositions be limited to a particular type and/or amount. Nonetheless, in one embodiment, the organic diol comprises an aliphatic diol, such as, without limitation, a simple diol. In one embodiment, the organic diol is exemplified by, but not limited to, propylene glycol, ethylene glycol, 1,3-butanediol, 1,7-heptanediol, 1,2-octanediol, 1,5-pentanediol and polyethylene glycol. In one embodiment, the composition comprises from 0.001 wgt. % to 5 wgt. % of the organic diol. In one embodiment, at least one organic diol in the composition is generally recognized as safe (GRAS).

In some embodiments, the composition further comprises an oxidizing agent, such as, but not limited to, an unstabilized oxidizing agent. While not intending to limit the oxidizing agent (whether stabilized or unstabilized) to a particular type and/or amount, in one embodiment, the oxidizing agent is exemplified by, but not limited to, bromine, sodium hyporchlorite, calcium hyporchlorite, chlorine dioxide, chlorine, hypochlorous acid, hydrogen peroxide, peroxyacetic acid, and ozone. In another embodiment, the composition comprises from 0.001 wgt. % to 30 wgt. % of the oxidizing agent.

In particular embodiments, the composition further comprises a surfactant. While not intending to restrict the type of surfactant, in one embodiment, the surfactant comprises an anionic surfactant exemplified by, but not limited to, sodium lauryl sulfate, ammonium lauryl sulfate, alkylbenzene sulfonic acid, sodium 2-ethylhexyl sulfate, and dioctyl sodium sulfosuccinate. In an alternative embodiment, the surfactant comprises a neutral surfactant exemplified by, but not limited to, octyl phenol ethoxylate, glyceryl monostearate, polyglyceryl-10 decaoleate, and lauryl lactyl lactate. In yet a further embodiment, the surfactant comprises a cationic surfactant exemplified by, but not limited to, cetrimonium bromide, cetylpyridinium chloride, benzalkonium chloride, cocamidopropyl betaine, ethylene oxide moiety, and propylene oxide moiety. Still in other embodiments, the surfactant comprises a linear alkylbenzene sulfonate, alcohol sulfate, alpha-olefin sulfonate, alcohol ethoxylate, nonylphenyl ethoxylate, alkylpolyglucoside, fatty alkanoamide, fatty amine oxide, sodium dioctylsulfosuccinate, dodecylbenzene sulfonic acid, dodecylbenzene sulfonic acid salt, sulfonated oleic acid sodium salt, sodium dodecylbenzene sulfonate, dodecyldiphenyloxidedisulfonic acid, and dodecyldiphenyloxidedisulfonic acid salt. It is not contemplated that the invention be limited to a particular concentration of surfactant. However, in some embodiments, the composition comprises from 0.001 wgt. % to 0.1 wgt. % of the surfactant.

Also without intending to limit the invention's compositions to any particular combination of acid, organic diol, oxidizing agent, and surfactant, in one embodiment, the composition is exemplified by, but not limited to, compositions AA, BB, CC, DD, xx1, xx2, xx3, and xx4. The invention also provides a concentrated solution and a diluted solution of any of the compositions disclosed herein, such as of compositions AA, BB, CC, DD, xx1, xx2, xx3, and xx4. In a particular embodiment, It is not intended to limit the temperature of the composition. Thus, in some embodiments, the composition is at a temperature from the freezing temperature of the composition to 120° C.

The invention additionally provides an aqueous composition comprising an a) acid, b) organic diol, and c) unstabilized oxidizing agent, wherein the composition (i) has acidic pH, and (ii) has antimicrobial activity. In a particular embodiment, the antimicrobial activity of (a) the acid, (b) the organic diol, (c) the oxidizing, (d) a combination of the acid and of the organic diol, (e) a combination of the acid and of the oxidizing agent, and (f) a combination of the organic diol and of the oxidizing agent, is lower than antimicrobial activity of a combination of the acid, of the organic diol and of the oxidizing agent. In particular embodiments, the composition further comprises d) a surfactant.

While not intending to limit the invention's compositions to any particular combination of acid, organic diol, unstabilized oxidizing agent and surfactant, in some embodiments, the composition is exemplified by, but not limited to, compositions A, B, C, D, E, F, G, H, I, J, K, L, M, N, O, x1a, x1, x2, x3, x4, x5, x6, x7, x8, x9, x10, x11, x12, x13, x14, x15, a1, a2, a3, a4 and a5. The invention additionally contemplates a concentrated solution and a diluted solution of any of the compositions disclosed herein. In some embodiments, at least one of the acid, the organic diol and the oxidizing agent is generally recognized as safe (GRAS).

In certain embodiments, (a) the oxidizing agent comprises hypochlorous acid, and (b) the rate of decrease in concentration of the hypochlorous acid in the presence of the diol is greater than in the absence of the diol. Preferred, but not limiting, embodiments, include those in which antimicrobial activity in the presence of the diol is greater than in the absence of the diol. In certain embodiments, the acidic pH is from pH 2 to pH 5.5. In yet other embodiments, the composition is at a temperature from the freezing temperature of the composition to 120° C.

The invention also provides an agricultural product having a surface film that comprises any of the compositions disclosed herein, including an a) acid that does not contain an —NH group and an —NH$_2$ group, and b) organic diol. In some embodiments, the film further comprises an oxidizing agent, such as an unstabilized oxidizing agent. In other embodiments, the film further comprises a surfactant. Certain embodiments include those where the film is edible, dry appearing and/or clear. In an alternative embodiment, the agricultural product is pre-harvest or post-harvest.

The invention additionally provides an agricultural product having a surface film that comprises an a) acid, b) organic diol, and c) unstabilized oxidizing agent. In some embodiments, the film further comprises d) a surfactant.

Also provided by the invention is a method for making an aqueous antimicrobial composition comprising an (a) acid that does not contain an —NH group and an —NH$_2$ group, and (b) organic diol, wherein the composition (i) has acidic pH and (ii) has antimicrobial activity. In one embodiment, the method comprises a) providing i) an acid that does not contain an —NH group and an —NH$_2$ group, and ii) an organic diol, and b) mixing the acid and the diol in water to produce an aqueous antimicrobial composition. In one embodiment, the method further comprises c) mixing an oxidizing agent in the aqueous antimicrobial composition. In particular embodiments, mixing with the oxidizing agent is in the absence or presence of an oxidizing agent stabilizer. In an alternative embodiment, the method further comprises c) mixing a surfactant in the aqueous antimicrobial composition. The invention also provides an aqueous antimicrobial composition produced by any of the methods described herein.

The invention additionally provides a method for making an aqueous antimicrobial composition comprising an a) acid, b) organic diol, and c) unstabilized oxidizing agent, wherein the composition (i) has acidic pH, and (ii) has antimicrobial activity. In one embodiments, the method comprises a) providing an i) acid, ii) organic diol, and iii) unstabilized oxidizing agent, b) mixing the acid and the diol in water to produce a first mixture, and c) mixing the oxidizing agent with the first mixture to produce an aqueous antimicrobial composition. In particular embodiments, the method further comprises mixing a surfactant in the aqueous antimicrobial composition. In alternative embodiments, the oxidizing agent comprises chlorine. The invention also provides an aqueous antimicrobial composition produced by any of the methods disclosed herein.

In yet another embodiment, the invention provides a method for reducing the number of microbes on a surface, comprising a) providing i) a first surface comprising a first number of microbes, and ii) an antimicrobially effective amount of any of the compositions described herein, and b) contacting the first surface with the composition under conditions that produce a contacted surface comprising a reduced number of the microbes compared to the first number of the microbes on the first surface in the absence of the contacting. In a particular embodiment, the composition comprises an (a) acid that does not contain an —NH group and an —NH$_2$ group, and (b) organic diol, wherein the composition (i) has acidic pH and (ii) has antimicrobial activity. The composition may further comprise an oxidizing agent, such as an unstabilized oxidizing agent, and/or a surfactant.

While not intending to limit the antimicrobial activity of any of the invention's compositions, in one embodiment, (A) the first surface comprises from 3-log to 8.78-log number of the microbes, (B) the contacting is for at least 2 minutes at a temperature of at least 34° F., and (C) the reduced number of the microbes comprises at least a 3-log reduction in the number of the microbes on the contacted surface compared to the first surface. In an alternative embodiment, the reduced number of the microbes comprises 100% reduction in the number of the microbes on the contacted surface compared to the first number of the microbes on the first surface.

It is not intended that the invention be limited to a particular antimicrobial effect on pathogenic versus non-pathogenic microbes. Nonetheless, in one embodiment, the first surface comprises a pathogenic microbe and a non-pathogenic microbe, and the reduced number of the microbes comprises a greater reduction in the number of the pathogenic microbe than in the number of the non-pathogenic microbe. In another embodiment, the pathogenic microbe and the non-pathogenic microbe comprise Gram-positive bacteria. In a particular embodiment, the pathogenic Gram-positive bacteria comprise *Staphylococcus aureus* and the non-pathogenic Gram-positive bacteria comprise *Lactobacillus* sp. In yet another alternative embodiment, the pathogenic microbe comprises Gram-negative bacteria and the non-pathogenic microbe comprises Gram-positive bacteria. Alternatively, the pathogenic Gram-negative bacteria are exemplified by, but not limited to, *Escherichia coli* and *Salmonella enterica*, and the non-pathogenic Gram-positive bacteria comprise *Lactobacillus* sp. In a further alternative, the pathogenic microbe comprises pathogenic bacteria and the non-pathogenic microbe comprises non-pathogenic bacteriophage. In yet another embodiment, the pathogenic bacteria comprise *Escherichia coli* and the non-pathogenic bacteriophage comprises bacteriophage T4. In a further embodiment, the pathogenic microbe comprises pathogenic virus and the non-pathogenic microbe comprises non-pathogenic bacteriophage. In another alternative embodiment, the pathogenic virus comprises Rhinovirus and the non-pathogenic bacteriophage comprises bacteriophage T4.

The invention's methods are not limited to the nature or number of steps other than the step of contacting a surface with the invention's compositions. Nonetheless, the invention's methods that use a composition comprising an (a) acid that does not contain an —NH group and an —NH$_2$ group, and (b) organic diol, wherein the composition (i) has acidic pH and (ii) has antimicrobial activity, may further comprise step c) drying the contacted surface to produce a dried surface comprising one or more of the acid and the organic diol. In an alternative embodiment, the method comprises c) washing the contacted surface under conditions that reduce the amount of one or more of the acid and the organic diol on the contacted surface.

Alternatively, the invention's methods that use a composition comprising an a) acid, b) organic diol, and c) unstabilized oxidizing agent, wherein the composition (i) has acidic pH, and (ii) has antimicrobial activity, may further comprise step c) drying the contacted surface to produce a dried surface comprising one or more of the acid, the organic diol, and the oxidizing agent. In an alternative embodiment, the method further comprises c) washing the contacted surface under conditions that reduce the amount of one or more of the acid, the organic diol, and the oxidizing agent on the contacted surface.

It is contemplated that any of the invention's methods wherein the surface is a surface of an agricultural product, the method further comprises c) storing the contacted agricultural product. In some embodiments, storing is at a chilling temperature, such as from 30° F. to 45° F.

The temperature at which the surface is contacted with the invention's compositions is not limited to any particular temperature. Thus, in one embodiment, contacting is at a temperature from the freezing temperature of the composition to 120° C.

Without limiting the type of surface that is contacted with the invention's compositions, in a particular embodiment, the surface is a surface of an agricultural product and the contacted surface has reduced discoloration compared to the first surface in the absence of the contacting. In a particular embodiment, the discoloration comprises pinking and the agricultural product is exemplified by, but not limited to, lettuce, cabbage, celery, and Bok Choy. In an alternative embodiment, the discoloration comprises browning and the agricultural product is exemplified by, but not limited to, lettuce, cabbage, celery, Bok Choy, potato, parsnip, avocado, apple, strawberry, spinach, meat, poultry and seafood.

The invention does not contemplate limiting the method of contacting a surface with the invention's compositions. However, in one embodiment, contacting comprises one or more of immersing, dipping, spraying, fogging, aerosoling, washing, and scrubbing the surface with the composition. In a particular embodiment, the contacting does not alter one or more of odor, texture and color of the surface.

It is not intended that the invention be limited to the type or source of the microbe against which the invention's compositions have antimicrobial activity. Thus, in one embodiment, the microbe comprises bacteria. In a particular embodiment, the bacteria comprise Gram-negative bacteria exemplified by, but not limited to, *Escherichia coli, Salmonella, Pseudomonas, Moraxella, Helicobacter, Stenotrophomonas, Bdellovibrio*, acetic acid bacteria, *Legionella*, alpha-proteobacteria, *Hemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, Salmonella typhi, Campylobacter*, and *Acinetobacter* baumanii. In another embodiment, the bacteria comprise Gram-positive bacteria exemplified by, but not limited to, *Bacillus, Listeria, Staphylococcus, Streptococcus, Enterococcus, Clostridium*, and Mollicutes. In particularly preferred embodiments, the Gram-positive bacteria are selected from the group of *Listeria monocytogenes, Staphylococcus aureus* and *Lactobacillus* sp.

In an alternative embodiment, the microbe comprises a fungus. In a particular embodiment, the fungus comprises a flagellated fungus selected from the group of Plasmodiophoromycetes, Chytridiomycota and Oomycetes. In an alternative embodiment, the fungus comprises a non-flagellated fungus selected from the group of Zygomycota, Ascomycota, Deuteromycetes and Basidiomycetes. In yet a further embodiment, fungus is selected from the group of *Aspergillus flavus, Septoria lycopersici*, and *Stachybotrys chartarum*.

In yet another alternative embodiment, the microbe comprises a virus. In a particular embodiment, the virus is selected from the group of rhinovirus, human papilloma virus, human immunodeficiency virus, hepatitis virus, Newcastle disease virus, cardiovirus, corticoviridae, cystoviridae, epstein-barr virus, filoviridae, hepadnviridae, hepatitis virus, herpes virus, influenza virus, inoviridae, iridoviridae, metapneumovirus, orthomyxoviridae, papovavirus, paramyxoviridae, parvoviridae, polydnaviridae, poxyviridae, reoviridae, rhabdoviridae, semliki forest virus, tetraviridae, toroviridae, vaccinia virus, and vesicular stomatitis virus. In another embodiment, the virus comprises a bacteriophage selected from the group of Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, and Cystoviridae. In particular embodiments, the bacteriophage comprises bacteriophage T4.

In a further embodiment, the microbe comprises a nematode, as exemplified by *Aphelenchoides fragariae*.

The invention is not limited to the type or source of surface that may be contacted with the invention's compositions. Thus in one embodiment, the surface is a surface of an agricultural product, exemplified by, but not limited to, vegetable, fruit, bulb, root, berry, herb, seed, meat, poultry, seafood, poultry egg, animal hide, and feather. In another embodiment, the surface is a surface of skin and/or of an inanimate object.

The invention further contemplates an agricultural product comprising a contacted surface that is produced by the steps of any of the methods described herein.

Also provided by the invention is a method for reducing discoloration of an agricultural product, comprising a) providing i) an agricultural product having a first surface, ii) an anti-discoloration effective amount of any of the compositions disclosed herein, and b) contacting the agricultural product with the composition under conditions that produce a contacted surface having reduced discoloration compared to discoloration of the first surface in the absence of the contacting.

BRIEF DESCRIPTION OF THE DRAWINGS

FIG. 1 shows the level of hypochlorous acid in solution, as determined by the DPD assay. (A) Composition "x1a" containing ortho-phosphoric acid 0.03 wgt. %, propylene glycol 0.02 wgt. %, hypochlorous acid 0.005 wgt. % at pH 4. (B) Chlorine solution containing ortho-phosphoric acid 0.001 wgt. % and hypochlorous acid 0.005 wgt. % at pH 7.

DEFINITIONS

To facilitate understanding of the invention, a number of terms are defined below.

The term "wgt. %" refers to the relative weight of two compounds when expressed as a percentage. For example, a solution containing 10 wgt. % of ortho-phosphoric acid propylene glycol dissolved in water refers to a solution prepared by diluting 10 grams of ortho-phosphoric acidpropylene glycol with water to a final weight of 100 grams.

"Logarithm" and "log" of a number, such as when used in reference to a concentration, cell number, etc., interchangeably refer to the power or exponent to which a base of 10 must be raised in order to produce the number. For example, 6-log means 1,000,000. Thus, a 3-log reduction means a 1,000 fold reduction.

"Aqueous" solution or composition refers to a solution or composition in which the solvent is water.

An "organic" chemical compound (e.g., organic acid, organic diol, organic oxidizer, organic solvent, etc.) is a chemical compound that contains carbon. In contrast, an "inorganic" chemical compound (e.g., inorganic acid, inorganic oxidizer, inorganic solvent, etc.) is a chemical compound that does not contain carbon.

"Microbe" and "microorganism" interchangeably refer to an organism that is too small to be seen by the naked human eye. Microbes include prokaryotes (such as bacteria, and virus (including bacteriophage), etc.), and eukaryotes (such as protists (including nematodes), animals, fungi, and plants). Microbes may be pathogenic or non-pathogenic.

"Pathogen" refers to an organism that causes a disease in a multicellular animal. In contrast, a "non-pathogen" is an organism that does not cause disease in an animal. "Animal" includes mammals (e.g., humans, non-human primates, murines, ovines, bovines, ruminants, lagomorphs, porcines, caprines, equines, canines, felines, aves, etc.), avians (e.g., chicken), amphibians (e.g., *Xenopus*), reptiles, etc.

The term "bacteria" refers to all prokaryotic organisms, including those within all of the phyla in the Kingdom Procaryotae. Bacteria include *Mycoplasma, Chlamydia, Actinomyces, Streptomyces*, and *Rickettsia*. Forms of bacteria include cocci, bacilli, spirochetes, spheroplasts, protoplasts, etc. Bacteria may be Gram-negative or Gram-positive. "Gram-negative" and "Gram-positive" refer to staining patterns with the Gram-staining process that is well known in the art (Finegold and Martin, Diagnostic Microbiology, 6th Ed. (1982), CV Mosby St. Louis, pp 13-15). "Gram-positive bacteria" are bacteria that retain the primary dye used in the Gram-stain, causing the stained cells to appear dark blue to purple under the microscope. "Gram-negative bacteria" do not retain the primary dye used in the Gram-stain, but are stained by the counterstain. Thus, Gram-negative bacteria appear red.

"Gram-negative bacteria" include the proteobacteria, exemplified by *Escherichia coli, Salmonella*, and other Enterobacteriaceae, *Pseudomonas, Moraxella, Helicobacter, Stenotrophomonas, Bdellovibrio*, acetic acid bacteria, *Legionella*, alpha-proteobacteria such as Wolbachia and many others. Gram-negative bacteria include bacilli that cause respiratory problems (such as *Hemophilus influenzae, Klebsiella pneumoniae, Legionella pneumophila, Pseudomonas aeruginosa*), urinary problems (*Escherichia coli, Proteus mirabilis, Enterobacter cloacae, Serratia marcescens*), and gastrointestinal problems (*Helicobacter pylori, Salmonella enteritidis, Salmonella typhi* and *Campylobacter*). Gram-negative bacteria associated with nosocomial infections include *Acinetobacter baumanii*, which cause bacteremia, secondary meningitis, and ventilator-associated pneumonia in intensive care units of hospital establishments.

"Gram-positive bacteria" include the phylum Firmicutes (exemplified by the genera *Bacillus, Listeria, Staphylococcus, Streptococcus, Enterococcus*, and *Clostridium*), and the Mollicutes (exemplified by *Mycoplasma* that lack cell walls and cannot be Gram stained). *Listeria monocytogenes* is a Gram-positive bacteria that is of particular concern in many ready-to-eat meat, poultry, seafood, and dairy processing chill brine applications.

The term "virus" refers to obligate, ultramicroscopic, intracellular parasites incapable of autonomous replication (i.e., replication requires the use of the host cell's machinery). Viruses are exemplified by, but not limited to, rhinovirus, human papilloma virus, human immunodeficiency virus, hepatitis virus, Newcastle disease virus, cardiovirus, corticoviridae, cystoviridae, epstein-barr virus, filoviridae, hepadnviridae, herpes virus, influenza virus, inoviridae, iridoviridae, metapneumovirus, orthomyxoviridae, papovavirus, paramyxoviridae, parvoviridae, polydnaviridae, poxyviridae, reoviridae, rhabdoviridae, semliki forest virus, tetraviridae, toroviridae, vaccinia virus, and vesicular stomatitis virus.

A "fungus" is a eukaryotic organism that is a member of the kingdom Fungi. Fungi are heterotrophic organisms possessing a chitinous cell wall. The majority of species grow as multicellular filaments called hyphae forming a mycelium. Some fungal species also grow as single cells. Fungi include "mold," which are microscopic fungi that grow in the form of multicellular filaments, called hyphae. Molds include dermatophytes (i.e., pathogenic fungus that infects the skin) exemplified by the genera *Epidermophyton, Microsporum* and *Trichophyton* (such as *Trichophyton rubrum* and *Trichophyton mentagrophytes*). *Trichophyton* can cause tinea pedis (athlete's foot) and/or tinea cruris (jock itch). Plant fungi include flagellated fungi and non-flagellated fungi.

Flagellated fungi include Plasmodiophoromycetes, Chytridiomycota and Oomycetes. Plasmodiophoromycetes include *Plasmodiophora brassicae* that causes club root of cabbage, and *Spongospora subterranean* that causes powdery scab of potatoes. Chytridiomycota include *Olpidium* spp. that infect pollen, *Physoderma maydis* that causes brown spot of corn leaves, and *Synchytrium* spp. that cause wart of potatoes. The Peronosporales group is exemplified by the late blight of potato fungus *Phytophthora infestans, Peronospora, Bremia, Plasmopara* and others that cause "downy mildews", the "damping off" fungi, *Pythium* spp., and the white rust fungi, *Albugo* spp.

Non-flagellated Fungi include Zygomycota, Ascomycota, Deuteromycetes and Basidiomycetes. Zygomycota include the Mucorales that are exemplified by members of the bread mold genus *Rhizopus*, and Hoanephora that causes blossom blight and decay of squash. Ascomycota include *Taphrina deformans* that causes peach leaf curl, and Nematospora that causes seed decay and root rot on cotton, Plectomycetes such as *Ophiostoma* (*Ceratocystis*), and *O. ulmi* that causes Dutch elm disease, Pyrenomycetes such as powdery mildews of the genus *Erysiphe* that is common on grasses, *Phyllactinia* on oaks and other trees, and *Uncinula* on grapes and other shrubs, Discomycetes such as *Sclerotinia* that causes stromatic rot of vegetables, and *Monilinia*, the cause of brown rot of peaches, and Loculoascomycetes such as Myriangiales that include *Elsinoe* species that cause citrus scab, and Dothideales that include *Capnodium* species that cause sooty molds of plants. Deuteromycetes include Ascomycetes such as species of *Alternaria, Bipolaris, Botrytis, Cercospora, Diplodia, Dreschlera, Exerohilum, Fusarium, Phoma, Phomopsis, Rhizoctonia*, and *Verticillium* that cause molds, blights, cankers, leaf spots, and root rots. Basidiomycetes include Uredinales, Exobasidiales, and Aphyllophorales that cause rusts, smuts, felt fungi, root rots, heart rots, and threadblights.

A "bacteriophage" is a virus that infects bacteria. Bacteriophages are classified in the families Myoviridae, Siphoviridae, Podoviridae, Tectiviridae, Corticoviridae, Lipothrixviridae, Plasmaviridae, Rudiviridae, Fuselloviridae, Inoviridae, Microviridae, Leviviridae, and Cystoviridae "Nematode" and "roundworm" interchangeably refer to a multicellular organism that is a member of the Phylum Nematoda. Exemplary nematodes that are agricultural pests include corn pests such as *Belonolaimus* (Sting Nematode), *Criconemoides* (Ring nematode), *Helicotylenchus* (Spiral Nematode), *Heterodera zeae* (Corn Cyst Nematode), *Hoplolaimus* (Lance Nematode), *Xiphinema* (Dagger Nematode), *Longidorus* (Needle Nematode), *Meloidogyne* (Root-Knot Nematode), *Pratylenchus* (Lesion Nematode), *Paratrichodorus* (Stubby-Root Nematode), *Tylenchorhynchus* (Stunt Nematode); potato pests such as *Meloidogyne chitwoodi* (Columbia Root-knot Nematode), *Globodera rostochiensis* (Golden Nematode), *Meloidogyne hapla* (Northern Root Knot Nematode), *Ditylenchus destructor* (Potato Rot Nematode), *Globodera pallida* (Pale Potato Cyst Nematode); soybean pests such as *Heterodera glycines* (Soybean cyst nematode) and *Belonolaimus* spp. (Sting nematode); sugar beet pests such as *Heterodera schachtii* (Sugar beet cyst nematode) and *Nacobbus aberrans* (False root-knot nematode); turf pests such as *Belonolaimus* species (Sting Nematode), *Hoplolaimus galeatus* (Lance Nematode), *Meloidogyne* species (Root-knot Nematodes) and *Criconemoides* species (Ring Nematode); trees and vines pests such as *Bursaphelenchus xylophilus* (Pine wilt nematode), *Tylenchulus semipenetrans* (Citrus nematode), *Radopholus similis* (Burrowing nematode), *Belonolaimus longicaudatus* (Sting nematode), *Xiphinema americanum* (Dagger nematode), *Mesocriconema xenoplax* (Ring nematode), *Meloidogyne hapla* (Root-knot nematode), *Tylenchorhynchus* spp. (Stunt nematode), *Rotylenchulus* spp. (Reniform nematode) and *Pratylenchus* spp. (Lesion nematode); ornamentals and garden vegetables pests such as *Aphelenchoides* spp. (Foliar nematodes), *Meloidogyne* spp. (Root-knot nematodes), *Ditylenchus dipsaci* (Stem and bulb nematode), and *Belonolaimus longicaudatus* (Sting nematode).

The term "surface" refers to one or more of the faces of a three-dimensional object, including surfaces that are visible to the naked eye (e.g., agricultural products, inanimate objects, etc.) and surfaces not visible to the naked eye (e.g., open stomata and damaged cells on a plant leaf surface).

"Agricultural product" refers to plant material and/or animal material that may be useful to man, as well as products derived directly or indirectly therefrom (e.g., cut flowers, cooked meat, etc.). Agricultural products include food products and non-food products.

"Food product" refers to an agricultural product that is "edible" (i.e., suitable for use as food) to at least one animal (e.g., human, livestock, etc.). For example, the invention's compositions may be edible when they are present as a film on a food product and when the type and/or amount of the components are generally recognized as safe (GRAS). Food products include "pre-harvest" and "post-harvest" products. Food products are exemplified by, but not limited to, fruits, vegetables, herbs, seeds, nuts, meat, poultry, seafood, poultry eggs, etc. Food products may be fresh or processed. "Fresh food product" refers to a food product that has not been cooked or frozen (i.e., exposed to temperatures higher or lower than room temperature, i.e., ambient temperature). For example, a "fresh" food product includes, but is not limited to a, raw food product, unprocessed food product, food product that has not been heated above ambient temperature, food product that has not been cooled below ambient temperature, food product that does not contain a preservative, and/or irradiated food product. A "fresh" food product may be "fresh frozen," "frozen fresh," and "freshly frozen," which are terms that interchangeably refer to a food product that is quickly frozen while still fresh. A "fresh" food product may be blanched, i.e., briefly scalded, before freezing to prevent nutrient breakdown. "Produce" is a fresh food product derived from a plant (e.g., fruit, vegetable, herb, seed, nut, leaf, stem, bulb). "Processed food product" refers to a food product that has been manipulated by man including a product that has been cut, chopped, sliced, peeled, ground, milled, irradiated, frozen, cooked (e, g, blanched and/or pasteurized), homogenized, germinated, washed, colored, waxed, hydrocooled, refrigerated, shelled, and/or had leaves, stems, or husks removed.

"Non-food product" refers to an agricultural product that is not edible to at least one animal. Non-food products include cut flowers, houseplants, animal hides, feathers, skin, shells, etc.

"Inanimate object" refers to an object not endowed with life or spirit such as equipment that is used for processing and/or harvesting agricultural products, hospital instruments and surfaces, surgical tools and apparatus, household items, buildings, tunnels, underpasses, overpasses, floors, doors (frames, door knobs, etc.), entrances, exits, ceilings, bathrooms and fixtures, furniture, wood, Teflon™, ultra high molecular weight (UHMW) polyethylene, ceramic tile, steel (e.g., stainless steel), cement, glass, paint (e.g., acrylic paint), and reverse osmosis (RO) membrane (i.e., semi permeable thin film composite membranes, referred to as TFC or TFM).

"Skin" refers to the integument of an animal separated from the body, with or without hair. The animal may be living or non-living. Skin may be on the outside of the body, tissue on the inside of the body, and/or tissue at or near openings on the body, including openings made surgically.

"Film" refers to a thin covering, coating or layer. A film may be "clear" i.e., transparent and/or translucent. Alternatively, the film may be "opaque." Films may be visible to the human naked eye or invisible to the human naked eye. A film may be "edible," i.e., is not toxic when ingested by an animal. To illustrate, an edible film containing one or more of the invention's compositions includes, without limitation, a film in which the components are listed as GRAS and/or FCC. A film may be "adherent," i.e., is not removed from a surface after rinsing with water for 1 minute. A liquid film may appear dry to the naked human eye.

"Bio-film" is a film containing an aggregation of microorganisms. Bio-films are characterized by structural heterogeneity, genetic diversity, complex community interactions, and an extracellular matrix of polymeric substances.

"Bio-load" and "biological load" refer to the waste output of organisms, plant matter, soil, extracts, and any other biological matter that is capable of changing the oxygenation rate of a fluid, e.g., water.

The terms "reduce," "decrease," and grammatical equivalents when in reference to a numerical value (e.g., number of cells, concentration, etc.) of any molecule (e.g., acid, diol, oxidizing agent, surfactant, etc.), and/or phenomenon (e.g., antimicrobial activity, microbial contamination, cell division, cell viability, discoloration, pinking, browning, etc.) in a first sample relative to a second sample, mean that the quantity of the numerical value in the first sample is lower than in the second sample by any amount that is statistically significant using any art-accepted statistical method of analysis. The reduction may be determined objectively and/or subjectively. In one embodiment, the quantity of the numerical value in the first sample is at least 10% lower than, at least 25% lower than, at least 50% lower than, at least 75% lower than, at least 90% lower than, at least 99% lower than, and/or 100% lower than the quantity of the numerical value in the second sample.

The terms "increase," and grammatical equivalents when in reference to a numerical value (e.g., number of cells, concentration, etc.) of any molecule (e.g., acid, diol, oxidizing agent, surfactant, etc.), and/or phenomenon (e.g., antimicrobial activity, microbial contamination, cell division, cell viability, discoloration, pinking, browning, etc.) in a first sample relative to a second sample, mean that the quantity of the numerical value in the first sample is higher than in the second sample by any amount that is statistically significant using any art-accepted statistical method of analysis. The increase may be determined objectively and/or subjectively. In one embodiment, the quantity of the numerical value in the first sample is at least 10% greater than, at least 25% greater than, at least 50% greater than, at least 75% greater than, and/or at least 90% greater than, and/or at least 100% greater than the quantity of the same molecule and/or phenomenon in the second sample.

"Acidic pH" refers to a pH less than 7.0, as exemplified by, but not limited to, a pH less than pH 6.5, less than pH 6.0, less than pH 5.5, less than pH 5.0, less than pH 4.5, less than pH 4.0, less than pH 3.5, less than pH 3.0, less than pH 2.5, less than pH 2.0, and less than pH 1.5. Thus, an acidic pH includes a pH from 2.0 to 6.0, from 2.0 to 5.0, from 2.0 to 4.0, and from 2.0 to 3.0.

Unless otherwise indicated, all numbers expressing quantities of ingredients, temperatures, microbes, reaction conditions, and so forth as used herein, are to be understood as being modified in all instances by the term "about," which refers to variation in the numerical quantity that can occur, for example, through typical measuring and liquid handling procedures used for making concentrates or using solutions in the real world; through inadvertent error in these procedures; through differences in the manufacture, source, or purity of the ingredients employed to make the compositions or carry out the methods; and the like. Accordingly, unless indicated to the contrary, the numerical parameters herein are approximations that may vary depending upon the desired properties sought to be obtained by the present invention. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

DESCRIPTION OF THE INVENTION

The invention provides antimicrobial compositions comprising one or more acid and one or more organic diol. In one embodiment, the invention's compositions have an acidic pH. The compositions may optionally further contain one or more oxidizing agent (including stabilized oxidizing agent and/or unstabilized oxidizing agent), and/or one or more surfactant. In particular embodiments, the acid lacks one or both of —NH group and —NH$_2$ group.

The invention's discovery of the invention's compositions that contain a combination of an acid and organic diol was premised, in part, on the surprising discovery of synergistic antimicrobial activity of this combination, including at acidic pH.

The invention's discovery of the invention's compositions that contain a combination of an acid, organic diol and an oxidizer was premised, in part, on the surprising discovery that adding an organic diol to an oxidizer in solution resulted in the ability to alter (increase or decrease) the pH of the solution independently of the bio-load, while also providing synergistic antimicrobial activity of the acid, organic diol and oxidizer.

In addition, inclusion of the organic diol unexpectedly reduced the undesirable odor when an oxidizer is included in the composition, particularly in the presence of bioload. This allowed, in one embodiment, the further addition of acids to the solution, which resulted in surprising synergistic antimicrobial activity by the acid, organic diol, and oxidizing agent. Furthermore, the inventor made the surprising observation that particular embodiments of the invention's compositions were capable of 100% reduction in microbial contamination at the chilling temperatures (e.g., from 30° F. to 40° F.) that are routinely used during standard processing steps for agricultural products, while not resulting in adverse effects on the odor, texture, color and/or appearance of the agricultural products. A further surprising aspect of the invention's compositions is that they had a broad spectrum of antimicrobial activity against bacterial, bacteriophage, viral, fungal and nematode microbes, using a wide variety of agricultural products and inanimate objects. Moreover, the invention's compositions surprisingly reduced discoloration (e.g., pinking and browning) of agricultural products. Yet another surprising property of the invention's compositions is that they showed a differential effect on pathogenic and non-pathogenic microbes, by reducing the number of pathogenic bacteria to a greater extent than the reduction of non-pathogenic bacteria and of non-pathogenic bacteriophage.

The invention's compositions have several additional advantages over antimicrobial compositions of the prior art. For example, in one embodiment, the invention's compositions are clear solutions, non-foaming during use, and continue to exhibit residual antimicrobial activity after drying.

In addition, the invention's compositions in one embodiment exhibit antimicrobial activity at acidic pH, thus advantageously allowing, in one embodiment, chlorine salts to remain in solution.

Moreover, after drying, the invention's compositions form a very thin film on the surface (including cracks and open stomata) of the treated products consisting of the composition's components. This film is edible because of its low toxicity to higher life forms, while continuing to exhibit antimicrobial activity, thus eliminating the need, and environmental and monetary cost, for rinsing off the invention's composition from the treated products (e.g., agricultural products). Moreover, a film can be placed on machines (or portions thereof such as cutting blades) that process agricultural products.

In addition, in one embodiment, the invention's compositions may be applied pre-harvest and post harvest of agricultural products, thus advantageously extending the period of exposure to antimicrobial activity, and resulting in increased shelf life.

Another advantage of the invention's compositions is that their antimicrobial activity is resistant to particulate loads, increased turbidity, and plant fluids. They also decrease turbidity in the solution, allow for lower processing temperatures (one to two ° F.), and decrease the incidence of ice crystal formation on the treated materials at refrigerated temperatures, thereby preserving surface quality.

A further advantage is that the invention's compositions are non-irritating when applied to skin as antiseptic even after 12 hours of contact, thus making them useful in medical applications. In one embodiment, compositions of the present invention can be applied directly to the skin. In another embodiment, the present invention contemplates surgical dressings, bandages and surgical tapes comprising one or more of the compositions set forth herein (see Tables below). Illustrative examples of such dressings and tapes include, but are not limited to, sheets of material, surgical swabs, gauze pads, closure strips, compress bandages, surgical tape, and the like. In a further embodiment, medical devices are contacted (and preferably coated, e.g., coated with a film) with compositions set forth herein (see Tables below). Such devices can be used both outside and in the body, including implantable medical devices (e.g., staples, shunts, stents, stitches, tubing, and the like). In one embodiment, teeth or dental products are contacted with compositions set forth herein. In yet another embodiment, contact lenses and related eye care articles are contacted with compositions set forth herein.

An additional advantage is that the invention's compositions may be made as concentrates and used in situ and ex situ. Yet another advantage is that they may be readily applied by standard methods such as spraying, dipping, wiping, etc., thus avoiding the need for costly modifications to existing commercial applications.

Thus, the invention's compositions are useful for antimicrobial applications in a variety of settings, such as before harvesting and/or at the point of harvesting and/or after harvesting of agricultural products (including food products, ornamental plants, etc.), at food production facilities including the disinfection of food processing equipment and harvesting equipment, in hospitals, offices, residences, etc. For example, the invention's compositions may be used pre-harvest for microbe reduction on living plants. Also, ice made of the invention's compositions may be used for cold storage of shellfish, fruits, vegetables and meats. The compositions also may be used to reduce undesirable odors from bacterial breakdown of food materials. Further utilities include reduction of microbial infection of skin, such as athlete's foot fungus "tinea pedis" (*Trichophyton*).

In addition, the invention's compositions may be used for rendering any type of surface resistant to mold, for cleaning and/or pre-treating such surfaces, and for rendering surfaces contaminated with potentially or actually hazardous microbes such as, but not limited to, mold spores, bacteria, viruses, protozoa and/or any biological warfare agents, safe to handle and/or safe to dispose of.

Additional advantages, surprising results and attributes of the invention are further described below under (A) Compositions and (B) Methods.

A. Compositions

The invention provides antimicrobial compositions comprising one or more acid and one or more organic diol. In one embodiment, the invention's compositions have an acidic pH. The compositions may optionally further contain one or more oxidizing agent (including stabilized oxidizing agent and/or unstabilized oxidizing agent), and/or one or more surfactant. In particular embodiments, the acid lacks one or both of —NH group and —NH$_2$ group.

The invention's compositions are exemplified by, but not limited to, compositions AA, BB, CC, DD, A, B, C, D, E, F, G, H, I, J, K, L, M, N and O in Table 1, which are illustrated by compositions xx1, xx2, xx3, xx4, x1a, x1, x2, x3, x4, x5, x6, x7, x8, x9, x10, x11, x12, x13, x14 and x15 in Table 2 and by compositions a1 to a5 in Tables 5 and 8.

TABLE 1

Exemplary compositions of the invention[1]

| Ref.[2] | Acid (wgt. %) | Diol (wgt. %) | Oxidizing Agent (wgt. %) | Surfactant (wgt. %) |
|---|---|---|---|---|
| AA | 0.001-0.9 ortho-Phosphoric acid | 0.001-2.0 Propylene glycol | | |
| BB[7] | 0.001-1.0 ortho-Phosphoric acid | 0.001-2.0 1,3-Butanediol | | |
| CC[8] | 0.003-5.0 Hydrochloric acid | 0.001-2.5 Propylene glycol | | |
| DD[7,8] | 0.003-5.0 Hydrochloric acid | 0.001-2.0 1,3-Butanediol | | |
| A[3] | 0.001-0.9 ortho-Phosphoric acid | 0.001-2.0 Propylene glycol | 0.005-2.9 Hypochlorous acid | |
| B | 0.001-0.9 ortho-Phosphoric acid | 0.001-3.0 Propylene glycol | 0.005-2.9 Hypochlorous acid and 0.05-0.9 Bromine | |
| C[4] | 20-30 ortho-Phosphoric acid | 3 Propylene glycol | 20 Hydrogen peroxide | |
| D[5] | 30 ortho-Phosphoric acid | 3 Propylene glycol | 20 Hydrogen peroxide | 0.01-1.9 Sodium lauryl sulfate |

TABLE 1-continued

Exemplary compositions of the invention[1]

| Ref.[2] | Acid (wgt. %) | Diol (wgt. %) | Oxidizing Agent (wgt. %) | Surfactant (wgt. %) |
|---|---|---|---|---|
| E | 0.001-0.9 ortho-Phosphoric acid | 0.01-3.0 Propylene glycol | 0.05-0.9 Hypochlorous acid and 0.05-0.9 Bromine | 0.01-1.9 Sodium lauryl sulfate |
| F | 0.001-0.05 ortho-Phosphoric acid | 0.01-3.0 Propylene glycol | 0.05-3.9 Peroxyacetic acid | |
| G | 0.001-0.05 ortho-Phosphoric acid | 0.01-3.0 Propylene glycol | 0.05-3.9 Peroxyacetic acid | 0.01-1.9 Octyl phenol ethoxylate |
| H | 0.001-0.05 ortho-Phosphoric acid | 0.01-3.0 Propylene glycol | 0.0003-1.9 Ozone | |
| I | 0.001-0.05 ortho-Phosphoric acid | 0.01-3.0 Propylene glycol | 0.0003-1.9 Ozone | 0.01-1.9 Octyl phenol ethoxylate |
| J | 1-6 ortho-Phosphoric acid | 0.1-0.6 Propylene glycol | 0.7-4 Hydrogen peroxide | |
| K[6] | 30 ortho-Phosphoric acid | 3 Propylene glycol | 20 Hydrogen peroxide | Less than 0.1 wgt. % of a surfactant to the concentrate when it is to be applied to surfaces |
| L | 0.3-5.0 Hydrochloric acid | 0.1-0.6 Propylene glycol | 0.7-4 Hydrogen peroxide | |
| M[6] | 20 Hydrochloric acid | 3 Propylene glycol | 20 Hydrogen peroxide | With or without 0.1 wgt. % of a surfactant |
| N | 0.9-8 Citric acid | 0.1-0.6 Propylene glycol | 0.7-4 Hydrogen peroxide | |
| O[6] | 35 Citric acid | 3 Propylene glycol | 20 Hydrogen peroxide | Addition of less than 0.1 wgt. % of a surfactant to the concentrate when it is to be applied to surfaces. |

[1]Water was used as solvent.
[2]pH of compositions other than concentrated compositions, is acidic.
[3]Concentrated compositions, such as compositions C, D, K, M, and O are diluted to a final concentration having an acidic pH less than pH 7.0.
[4]Composition A is food-safe and does not need to be rinsed off.
[5]Composition C is a concentrated antimicrobial composition that has antimicrobial effects when diluted to about one hundred to one in potable water, is food-safe and does not need to be rinsed off.
[6]Composition D is a concentrated antimicrobial composition that has antimicrobial effects when diluted to about one hundred to one in potable water, is food-safe and does not need to be rinsed off.
[7]Compositions K, M and O are concentrated antimicrobial compositions.
[8]With higher concentrations of 1,3-butanediol, the treated material had a slight odor.
[9]Compositions CC and DD killed *Lactobacillus*, and broad leaf material bleached quicker than with compositions AA and BB.

The exemplary compositions in Table 1 above are illustrated by compositions xx1, xx2, xx3, xx4, x1a, x1, x2, x3, x4, x5, x6, x7, x8, x9, x10, x11, x12, x13, x14 and x15 in Table 2 below (See also Tables 5 and 8).

TABLE 2

Additional Exemplary compositions of the invention.

| Ref.[1] | Sub Ref.[2] | Acid (wgt. %) | Diol (wgt. %) | Oxidizing Agent (wgt. %) | Surfactant (wgt. %) | pH[9] |
|---|---|---|---|---|---|---|
| AA | xx1 | 0.035 ortho-Phosphoric acid | 0.02 Propylene glycol | | | |
| BB | xx2 | 0.03 ortho-Phosphoric acid | 0.012 1,3-Butanediol | | | |
| CC | xx3 | 0.01 Hydrochloric acid | 0.018 Propylene glycol | | | |
| DD | xx4 | 0.008 Hydrochloric acid | 0.005 1,3-Butanediol | | | |

TABLE 2-continued

Additional Exemplary compositions of the invention.

| Ref.[1] | Sub Ref.[2] | Acid (wgt. %) | Diol (wgt. %) | Oxidizing Agent (wgt. %) | Surfactant (wgt. %) | pH[9] |
|---|---|---|---|---|---|---|
| A | x1a | 0.03 ortho-Phosphoric acid | 0.02 Propylene glycol | 0.005 Hypochlorous acid | | 4 |
| A | x1 | 0.08 ortho-Phosphoric acid | 0.09 Propylene glycol | 0.05 Hypochlorous acid | | 3-4.1 |
| B | x2 | 0.08 ortho-Phosphoric acid | 0.09 Propylene glycol | 0.01 Hypochlorous acid and 0.05 Bromine | | 4-5.5 |
| C[3] | x3 | 21 ortho-Phosphoric acid | 3 Propylene glycol | 20 Hydrogen peroxide | | 0.5-1 |
| D[4] | x4 | 30 ortho-Phosphoric acid | 3 Propylene glycol | 20 Hydrogen peroxide | 0.01 Sodium lauryl sulfate | 0.5-1.5 |
| E[5] | x5 | 0.07 ortho-Phosphoric acid | 0.1 Propylene glycol | 0.007 Hypochlorous acid and 0.08 Bromine | 0.03 Sodium lauryl sulfate | 3.3-4.5 |
| F | x6 | 0.003 ortho-Phosphoric acid | 0.1 Propylene glycol | 0.5 Peroxyacetic acid | | 3-4 |
| G | x7 | 0.003 ortho-Phosphoric acid | 0.14 Propylene glycol | 0.5 Peroxyacetic acid | 0.015 octyl phenol ethoxylate | 3-4 |
| H | x8 | 0.02 ortho-Phosphoric acid | 0.1 Propylene glycol | 0.001 Ozone | | 5-6 |
| I | x9 | 0.02 ortho-Phosphoric acid | 0.12 Propylene glycol | 0.001 Ozone | 0.015 octyl phenol ethoxylate | 5.5-6.5 |
| J | x10 | 1 ortho-Phosphoric acid | 0.1 Propylene glycol | 2.1 Hydrogen peroxide | | less than 2.0 |
| K[6] | x11 | 30 ortho-Phosphoric acid | 3 Propylene glycol | 20 Hydrogen peroxide | 0.001 Cetylpyridinium chloride | — |
| L | x12 | 0.3 Hydrochloric acid | 0.1 Propylene glycol | 3 Hydrogen peroxide | | less than 2.0 2.0 |
| M[7] | x13 | 20 Hydrochloric acid | 3 Propylene glycol | 20 Hydrogen peroxide | | — |
| N | x14 | 1 Citric acid | 0.3 Propylene glycol | 2 Hydrogen peroxide | | less than 2.0 |
| O[8] | x15 | 35 Citric acid | 3 Propylene glycol | 20 Hydrogen peroxide | 0.001 sodium lauryl sulfate | — |

[1]Composition reference letter corresponds to the same reference letter in Table 1.
[2]Composition sub-reference lettering (e.g., x1) refers to an exemplary composition within the range of concentrations of the reference composition (e.g., composition A).
[3]Composition C-x3 is a concentrated antimicrobial composition.
[4]Composition D-x4 is a concentrated antimicrobial composition, and is preferably prepared by first mixing sodium lauryl sulfate with propylene glycol.
[5]Composition E-x5 is preferably prepared by first mixing sodium lauryl sulfate with propylene glycol.
[6]Composition K-x11 is a concentrated antimicrobial composition.
[7]Composition M-x13 is a concentrated antimicrobial composition.
[8]Composition O-x15 is a concentrated antimicrobial composition.
[9]pH at 34° F. Concentrated compositions are diluted to a working concentration having an acidic pH less than 7.0.

The antimicrobial activity of the exemplary compositions x1 to x15 is shown in Table 6 on bacterial, bacteriophage, viral, fungal and nematode microbes, using a wide variety of agricultural products (including leafy vegetables, fruiting and flowering vegetables, podded vegetables, bulb and stem vegetables, root and tuberous vegetables, Rosaceae family fruits, Bramble fruits, berries, Asian fruit, North America fruit, raw meat, raw poultry, raw seafood, fresh seeds and nuts, eggs, fresh herbs, dried herbs, animal hides, feathers) and inanimate objects (such as those encountered in hospitals, food processing plants, residential buildings, office buildings, etc.). In addition, the antimicrobial activity of the exemplary compositions a1 to a5 is shown in Tables 5 and 8 on the highly pathogenic *E. coli*.

The components of the invention's compositions include those that are approved and not approved by the Food and Drug Administration (FDA) for one or more uses, including, but not limited to, compounds that are generally recognized as safe (GRAS) and/or food grade compounds (FCC) and/or registered with the Environmental Protection Agency (EPA).

The terms "generally recognized as safe" and "GRAS" when in reference to a compound refer to each of the substances in 21 C.F.R., §182 and §184, approved before 1958 by the FDA and/or USDA, items published in the Federal Register, as well as other compounds (even if not on the GRAS list) that are accepted in the industry as safe for one or more uses by an animal, including by a human. As used herein, "food grade" and "FCC" refer to the Food Chemical Codex (FCC) that serves as a guide for food grade quality consistent with good manufacturing practices and is published by U.S. Pharmacopeia (USP). For example, and without limitation, organic diols approved by the FDA and within the scope of the invention include propylene glycol (1,2-Propanediol), 1,3-butanediol, 1,2-ocatnediol, 1,5-pentanediol, and polyethylene glycol. Organic diols within the scope of the invention that are not yet approved by the FDA include ethylene glycol and 1,7-heptanediol.

The invention's compositions may contain one or more acid. An "acid" is a chemical compound that, when dissolved in water, gives a solution with a hydrogen ion activity greater than in pure water, i.e. has an acidic pH. Acids may be organic or inorganic. Organic acids are acids that contain carbon. Inorganic acids, also referred to as mineral acids, are acids that do not contain carbon. The Chemical Abstracts Service ("CAS"), Columbus, Ohio, USA, provides a comprehensive repository for data on organic and inorganic acids. Organic acids include, but are not limited to, hydroxyethanoic acid (CAS 79-14-1), citric acid (CAS 5949-29-1), ascorbic acid (CAS 50-81-7), lactic acid (CAS 50-21-5), malic acid (CAS 617-48-1), octenic acid (CAS 1871-67-6), oxalic acid (CAS 144-62-7), ursolic acid (CAS 77-52-1), and salts thereof. Inorganic acids include, but are not limited to, ortho-phosphoric acid (CAS 7664-38-2), chromic acid (CAS 1308-38-9), hydrobromic acid (CAS 10035-10-6), hydrochloric acid (also known as muratic acid) (CAS 7647-01-0), nitric acid (CAS 7697-37-2), sulfuric acid (CAS 7664-93-9) and salts thereof. Other acids contemplated within the scope of the invention include, without limitation, acetic acid, adipic acid, benzoic acid, glutaric acid, isoascorbic acid, mandelic acid, propionic acid, salicylic acid, sorbic acid, succinic acid, tartaric acid (Koefod U.S. Pat. No. 7,090,882), sodium acid pyrophosphate, acidic sodium hexametaphosphate, ethylenediaminetetraacetic acid and salts thereof (Andrews et al., U.S. Pat. No. 5,490,992). Because of their low solubility in water, octenic acid and ursolic acid may first be dissolved in an organic solvent (e.g., glycol, diol, ethanol at a temperature equal to or greater than 100° F., etc.) before mixing with water. Nitric acid at some concentrations may be toxic to humans, which makes its use on foodstuffs less desirable than other acids. Oxalic acid and chromic acid at some concentrations react with some materials, such as steel, so their use in cleaning equipment may be less desirable than other acids. In one embodiment, the acid lacks —NH groups and/or —NH$_2$ groups (e.g., is not a sulfamic acid).

In some embodiments, the amount of acid in the invention's concentrated compositions may be from 2 to 50 wgt. %, preferably from 10 to 35 wgt. %, and more preferably from 20 to 30 wgt. %. In particular embodiments, the concentrate is typically diluted with water to provide an acid concentration of from 0.001 to 2 wgt. %, preferably from 0.003 to 1 wgt. %, and more preferably from 0.01 to 0.10 wgt. %.

The invention's compositions may contain one or more organic diol. A "diol" or "glycol" is a chemical compound containing two hydroxyl (—OH) groups. A diol may be a vicinal diol or a geminal diol, including an aliphatic diol. A vicinal diol has hydroxyl groups bonded to adjacent atoms, e.g., ethylene glycol and propylene glycol. A geminal diol has hydroxyl groups bonded to the same atom, e.g., methanediol (H$_2$C(OH)$_2$), 1,3-butanediol, bisphenol A, etc. Organic diols may contain a branched chain or an unbranched chain of carbon atoms. Organic diols are preferably aliphatic diols (i.e., an organic diol composed of carbon and hydrogen and does not contain an aromatic ring), and more preferably simple aliphatic diols. A "simple aliphatic diol" is an aliphatic diol in which all the carbon atoms are covalently bonded to only hydrogen, and is exemplified by ethylene glycol, propylene glycol, 1,3-butanediol, etc. In contrast, a "complex aliphatic diol" is an aliphatic diol in which at least one carbon atom is covalently bonded to one or more atoms other than hydrogen. Thus, a complex aliphatic diol may contain —COOH, —NH$_2$, etc. In some embodiments, organic diols may contain one or more ether group (glycol ether) and/or one or more ester group (glycol ester), including monoesters and diesters. In another embodiment, organic diols may have one hydroxyl group esterified with a saturated and/or unsaturated aliphatic acid other than benzoic acid, and the other hydroxyl group esterified with the same or different saturated and/or unsaturated aliphatic acid other than benzoic acid. Exemplary organic diols include, without limitation, propylene glycol (CAS 57-55-6), ethylene glycol (CAS 107-21-1), 1,3-butanediol (CAS 107-88-0), 1,7-heptanediol (CAS 629-30-1), 1,2-octanediol (CAS 1117-86-8), 1,5-pentanediol (CAS 111-29-5) and polyethylene glycol (CAS 25322-68-3). In some embodiments, organic diols contain from 2 to 20, such as from 2 to 10, and/or such as from 2 to 5 carbon atoms. For example, the diol ethylene glycol contains 2 carbon atoms, 1,3-butanediol contains 4 carbon atoms, 1,5-pentanediol contains 5 carbon atoms, 1,7-heptanediol contains 7 carbon atoms, and 1,2-octanediol contains 8 carbon atoms.

In some embodiments, the amount of organic diol in the invention's concentrated compositions may be from 2 to 5 wgt. %, preferably from 3 to 4 wgt. %, and more preferably 3 wgt. %. In particular embodiments, the concentrate is typically diluted with water to provide an organic diol concentration of from 0.01 to 1 wgt. %, preferably from 0.09 to 0.3 wgt. %, and more preferably from 0.09 to 0.15 wgt. %.

The invention's compositions may contain one or more oxidizing agent. "Oxidizing agent," "oxidant" and "oxidizer" are interchangeably used to refer to a chemical compound that transfers oxygen atoms or gains electrons in a redox chemical reaction. In both cases, the oxidizing agent becomes reduced in the process. Exemplary oxidizing agents include, without limitation, bromine (CAS 7726-95-6), hypochlorous acid (CAS 7790-92-3, also referred to as IUPAC name chloric (I) acid), hydrogen peroxide (CAS 7722-84-1), peroxyacetic acid (PAA) (CAS 79-21-0), and ozone (CAS 10028-15-6). Hypochlorous acid cannot be isolated in pure form, but can be derived from, without limitation, sodium hyporchlorite, calcium hyporchlorite, chlorine dioxide and chlorine. Further oxidizing agents include sodium bromide, peracetic acid, chlorine dioxide, sodium hypochlorite, hydrogen peroxide (Bautista U.S. Pat. No. 6,045,846) and ozone. Ozone may be introduced into a fluid using methods known in the art (Conners et al., U.S. Pat. No. 6,086,833).

In preferred embodiments, the invention's compositions contain more than one oxidizer to produce a greater reduction in antimicrobial activity and/or in exposure times when compared to single oxidizers in order to obtain the same antimicrobial activity.

In some embodiments, the amount of oxidizer in the invention's concentrated compositions may be from 2 to 30 wgt. %, preferably from 10 to 30 wgt. %, and more preferably from 10 to 20 wgt. %. In particular embodiments, the concentrate is typically diluted with water to provide an oxidizer concentration of from 0.01 to 5 wgt. %, preferably from 0.001 to 3 wgt. %, and more preferably from 0.01 to 1 wgt. %. For example, levels of hypochlorous acid and hypochlorite are reported as $Cl_2$, using the standard DPD (N,N-diethyl-p-phenylenediamine) colorimetric test method (Hach Chemical Co., Loveland Colo.), described in Harp, U.S. Pat. No. 5,362,650 and Kroll, U.S. Pat. No. 6,180,412, by employing standard instruments, such as model number 5870000 pocket colorimeter II "2."

In contrast to the art (e.g., Williams, U.S. Patent Application 20060003023), in particular embodiments, the invention's compositions contain an "unstabilized oxidizer" ("USOX"), i.e., contain an oxidizing agent in the absence of an oxidizing agent stabilizer. A "compound that stabilizes an oxidizing agent" and "oxidizing agent stabilizer" interchangeably refer to a compound that reduces the rate of decrease in concentration of an oxidizing agent, such as that resulting from degradation of the oxidizer. Oxidizing agent stabilizers include, for example, sulfamic acid, alkali metal sulfamate (Williams, U.S. Patent Application 20060003023), amide derivatives of carbonic acid, hydrogen cyanide, carboxylic acid, amino acid, sulfuric acid, phosphoric acid, boric acid, urea, thiourea, creatinines, cyanuric acids, alkyl hydantoins, mono-ethanolamine, di-ethanolamine, organic sulfonamides, biuret, sulfamic acid and salts thereof, organic sulfamic acid, melamine (Shim et al., U.S. Pat. Nos. 6,478,972 and 6,533,958).

Oxidizers are unstable, and their rate of oxidation may change (i.e., increase or decrease) and may become uncontrolled, resulting in depletion of the oxidizing agent in a short period of time (such as less than 6 hours, Example 9). To avoid this problem, the prior art, such as Self et al., U.S. Pat. No. 3,328,294, discloses a stabilized oxidizer ("SOX") produced by reacting the unstabilized oxidizer NaOBr with an equal molar ratio of the stabilizer sulfamic acid. They disclose that the reaction does not go un-controlled and the stabilized oxidizer may linger for days. Because of these characteristics they caution against the use of their compositions on foods and in potable water.

In contrast to the prior art, particular embodiments, the invention uses unstabilized oxidizers in order to take advantage of newer technology and increase the log microbial kill rate. It is the inventor's view that unstabilized oxidizers provide an instantaneous reaction in a process stream or on contacting a surface, a reduction in toxicity to humans and animals, an almost immediate kill of contacted microbes, shorter processing time, instantaneous concentration control at product contact points, and take advantage of new control systems for fast automatic control of active ingredients.

The invention's compositions may contain one or more surfactant. A "surfactant" is a chemical compound that lowers the surface tension of a liquid, allowing easier spreading of the liquid, and thereby acting as a wetting agent. In one embodiment, a surfactant is an organic compound that is amphiphilic, meaning that it contains one or more hydrophobic groups ("tails") and one or more hydrophilic groups ("heads"). Surfactants may be anionic, neutral or cationic. "Anionic surfactants" are surfactants that dissolve in water to release an anion, and include, for example, sodium lauryl ether sulfate, also referred to as sodium lauryl sulfate (CAS 009004-82-4), ammonium lauryl sulfate (CAS 2235-54-3), alkylbenzene sulfonic acid (CAS 27176-87-0), sodium 2-ethylhexyl sulfate (CAS 126-92-1), and dioctyl sodium sulfosuccinate (Andrews et al, U.S. Pat. No. 5,490,992). "Neutral surfactants" are surfactants that dissolve in water without releasing an anion or cation, and include, without limitation, octyl phenol ethoxylate (CAS 9002-93-1), glyceryl monostearate (CAS 31566-31-1), polyglyceryl-10 decaoleate (CAS 011094-60-3), and lauryl lactyl lactate (CAS 910661-93-7). "Cationic surfactants" are surfactants that dissolve in water to release a cation, and include the exemplary cetrimonium bromide (CAS 57-09-0), cetylpyridinium chloride (CAS 123-03-5), benzalkonium chloride (CAS 8001-54-5), and cocamidopropyl betaine (CAS 86438-79-1). Additional examples of surfactants include those that contain ethylene oxide moieties and/or propylene oxide moieties. Yet more examples of surfactants include linear alkylbenzene sulfonates, alcohol sulfates, alpha-olefin sulfonates, alcohol ethoxylates, nonylphenyl ethoxylates, alkylpolyglucosides, fatty alkanoamides, fatty amine oxides, sodium dioctylsulfosuccinate, dodecylbenzene sulfonic acid and salts thereof, the sodium salt of sulfonated oleic acid, sodium dodecylbenzene sulfonate, dodecyldiphenyloxidedisulfonic acid and salts thereof (Koefod et al., U.S. Pat. No. 7,090,882, Andrews et al., U.S. Pat. No. 5,490,992).

In some embodiments, the amount of surfactant in the invention's concentrated compositions may be from 0.05 to 0.5 wgt. %, preferably from 0.01 to 0.03 wgt. %, and more preferably from 0.01 to 0.15 wgt. %. In particular embodiments, the concentrate is typically diluted with water to provide a surfactant concentration of from 0.01 to 0.05 wgt. %, preferably from 0.001 to 0.005 wgt. %, and more preferably from 0.001 wgt. % to 0.03 wgt. %.

The invention additionally provides compositions comprising a concentrated solution of any of the compositions disclosed herein. A "concentrate" of a first composition refers to a compositions that contains the same components and the same ratio of these components (relative to each other) as in the first composition, wherein the amount of each component in the first composition is multiplied by the same fold factor to yield the amount of that component in the concentrated composition. The fold factor may be from 2 to 100,000, from 5 to 10,000, from 10 to 1,000, and from 100 to 500. For example, for a composition containing 4 wgt. % component A and 6 wgt. % component B, a 2-fold concentrate of this composition contains 8 wgt. % component A and 12 wgt. % component B, and a 3-fold concentrate of this composition contains 12 wgt. % component A and 18 wgt. % component B. Concentrates may be used directly or diluted. They provide ease of handling and shipping (because of smaller volumes). Exemplary concentrates are compositions C, D, J, K, M, O in Table 1, as exemplified by compositions x3, x10, x11, x13 and x15 of Table 2.

The invention also contemplates compositions comprising diluted solutions of any of the compositions disclosed herein. A "diluted" solution of a first composition refers to a compositions that contains the same components and the same ratio of these components (relative to each other) as in the first composition, wherein the amount of each component in the first composition is divided by the same fold factor to yield the amount of that component in the concentrated composition. The fold factor may be from 2 to 100,000, from 5 to 10,000, from 10 to 1,000, and from 100 to 500. For example, for a composition containing 4 wgt. % component A and 6 wgt. % component B, a 2-fold dilution of this composition contains 2 wgt. % component A and 3 wgt. % component B. Diluted solutions may be used directly or further diluted. Exemplary diluted solutions are compositions A, B, E, F, G, H, I, L, N, O in Table 1, as exemplified by compositions xx1, xx2, xx3, xx4, x1a, x1, x2, x4, x5, x6, x7, x8, x9, x12, x14 and in Table 2 and by compositions a1 to a5 of Tables 5 and 8.

The invention's compositions may be prepared by adding and mixing the acid alone into water, followed by adding and mixing in the diol, and then adding and mixing in the oxidizing agent. Surfactant may be subsequently added and mixed in. The compositions may be compounded at temperatures between the freezing point and the boiling point of the solvent (e.g., water) used.

When making concentrates, the diol and acid may be mixed together in concentrated quantities, followed by the surfactant, if desired, for delivery to a mixture of oxidizer and solvent (e.g., water). Alternatively, the diol and oxidizer may be mixed together in concentrated quantities for delivery to a mixture of acid and solvent (e.g., water). Concentrates may be stored for more than 1 week.

The invention's compositions may be used in a variety of ways as further described below.

B. Methods

In one embodiment, the invention's compositions have antimicrobial activity and may be used in methods for reducing the number of microbes on a surface, comprising (a) providing (i) a first surface comprising microbes, (ii) an antimicrobially effective amount of any of the invention's compositions, and b) contacting the surface with the composition under conditions that produce a contacted surface comprising a reduced number of the microbes compared to the number of the microbes on the first surface in the absence of the contacting step.

The term "antimicrobial" and "antimicrobial activity" when in reference to a compound refers to a compound that reduces the number of and/or rate of growth of a microbe compared to the number and/or rate of growth of the microbe in the absence of the compound. In one embodiment, the number of and/or rate of growth of a microbe in the presence of an antimicrobial compound is at least 10% lower than, at least 25% lower than, at least 50% lower than, at least 75% lower than, at least 90% lower than, at least 99%, and/or at least 100% lower than the number of and/or rate of growth of the microbe in the absence of the antimicrobial compound. In another embodiment, a 9-log number of microbe is reduced by at least 3-log, at least 5-log, at least 7-log, and/or at least 9-log in the presence of the antimicrobial compound.

An "antimicrobially effective amount" of a compound or composition refers to an amount of the compound or composition that has antimicrobial activity, including microbistatic amounts and microbicidal amounts.

"MIC" and "minimum inhibitory concentration" refer to the lowest concentration that is microbistatic under a specific set of conditions.

"MBC" and "minimum biocidal concentration" refer to the lowest concentration that is microbicidal under a specific set of conditions.

An antimicrobial can be antibacterial, antifungal, antiviral and/or antinematode. An antimicrobial can be microbistatic, microbicidal, or both. An antimicrobial is "microbistatic" (e.g., bacteriostatic, fungistatic, etc.) if it reduces cell division by an amount less than 100%, without or without reducing cell viability. An antimicrobial is "microbicidal" (e.g., bactericidal, fungicidal, etc.) if it reduces cell viability by 100%, i.e., causes 100% cell death. Cell death is commonly detected by the absence of cell growth in liquid growth medium (e.g., absence of turbidity) or on a solid surface (e.g., absence of colony formation on agar). A "sterilizer," "sanitizer" and "disinfectant" are microbicidal. In contrast, a "preservative" is microbistatic. Certain microbistatic compositions are not bactericidal at any concentration.

Those of skill in the art know that a composition may have microbistatic or microbicidal activity by altering the concentration of its components, temperature, and contact time with a surface. For example, a composition that is microbistatic at a given concentration may be microbicidal at a higher concentration. Also, a composition that is microbistatic at a given temperature may be microbicidal at a higher temperature. Similarly, a composition that is microbistatic at a particular contact time may be microbicidal at a longer contact time with a surface.

Methods for determining antimicrobial activity are known in the art, e.g., Andrews et al., U.S. Pat. No. 5,490,992, Bailey et al., U.S. Pat. No. 4,107,192 and disclosed herein. For example, one assay involves exposing a bacterial strain (e.g., Escherichia coli) to a test composition on a particular substrate (e.g., an agricultural product) at a predetermined bacterial level in a culture media at an appropriate temperature. After a sufficient amount of contact time, an aliquot of a sample containing the exposed bacteria is collected, diluted and plated on agar. The plated sample of bacteria is then incubated for about forty eight (48) hours and the number of viable bacterial colonies growing on agar is counted. Once colonies have been counted the reduction in the number of bacteria caused by the test composition is determined. Reduction in bacteria is typically reported as the difference between the $\log_{10}$ of the initial inoculant's count and the $\log_{10}$ of the inoculant's count after exposure to the test composition. Assays may also be subjective, such as by visually observing a difference in the amount of spoilage of agricultural products.

The invention's compositions exhibit surprising synergistic activity with respect to, for example, antimicrobial activity of their components. "Synergistic" activity of a combination of two or more components means that the activity of the combination of two or more components is greater than the activity of each component alone. Without intending to limit the invention to any particular method of calculation, in one embodiment, synergy may be determined using the industrially accepted method described by Kul et al., Applied Microbiology 9:538-541 (1961) (see also Williams, U.S. Patent Application 20060003023), using the ratio determined by the formula:

$$Q_a/Q_A + Q_b/Q_B = \text{Synergy Index ("SI") wherein:}$$

$Q_A$=concentration of compound A (first component) in ppm, acting alone, which produced an end point (MIC or MBC of Compound A).

$Q_a$=concentration of compound A in ppm, in the mixture, which produced an end point.

$Q_B$=concentration of compound B (second component) in ppm, acting alone, which produced an end point (MIC or MBC of Compound B).

$Q_b$=concentration of compound B in ppm, in the mixture, which produced an end point. When the sum of $Q_a/Q_A$ and $Q_b/Q_B$ is greater than one, antagonism is indicated. When the sum is equal to one, additivity is indicated, and when less than one, synergism is demonstrated. The lower the SI, the greater the synergy shown by that particular mixture.

Thus, in one embodiment, synergy of the combination of acid and organic diol is obtained where the amount of each of the acid alone and of the organic diol alone has lower antimicrobial activity compared to the antimicrobial activity of a combination of the acid and the organic diol. In another embodiment, synergy of the combination of acid, organic diol and oxidizing agent is obtained where the amount of each of (a) the acid alone, (b) the organic diol alone, (c) the oxidizing agent alone, (d) combination of the acid and the organic diol, (e) combination of the acid and the oxidizing agent, and (f) combination of the organic diol and the oxidizing agent, has lower antimicrobial activity compared to the antimicrobial activity of a combination of the acid, the organic diol and the oxidizing agent.

For example, Table 3A shows antimicrobial synergy of propylene glycol and phosphoric acid, synergy of propylene glycol, phosphoric acid and hydrogen peroxide, and synergy of propylene glycol, phosphoric acid, hydrogen peroxide and sodium lauryl sulfate.

Also, Table 4 shows antimicrobial synergy of two components when compared to single components of Table 3A.

In another example, data herein shows synergistic antimicrobial activity of the components of composition "a1" that contains hypochlorous acid 0.01 wgt. %, phosphoric acid 1 wgt. %, and propylene glycol 2 wgt. %.

In particular, Table 3B shows that 180 minute treatment of spinach with each of hypochlorous acid 0.01 wgt. %, phosphoric acid 1 wgt. % and propylene glycol 2 wgt. % alone in water causes a 5.01-log, 4.13-log, and 3.98-log reduction, respectively, in a 6.87-log $E.$ $coli$ inoculum. Table 4 shows similarly low antimicrobial activity by a combination of two components of hypochlorous acid 0.01 wgt. % and phosphoric acid 1 wgt. %, which resulted in a 4.9-log reduction in a 6.87-log $E.$ $coli$ inoculum. In contrast, Table 5 shows that 180 minute treatment of spinach with the combination "a1" that contained hypochlorous acid 0.01 wgt. %, phosphoric acid 1 wgt. %, and propylene glycol 2 wgt. % resulted in a 6.57-log reduction in a 6.57-log $E.$ $coli$ inoculum.

Similarly, Table 3B shows that 180 minute treatment of spinach with each of bromine 0.08 wgt. %, phosphoric acid 1 wgt. % and propylene glycol 2 wgt. % alone caused a 4.44-log, 4.13-log, and 3.98-log reduction, respectively, in a 6.87-log $E.$ $coli$ inoculum. Table 4 shows similarly low antimicrobial activity by a combination of two components of bromine 0.08 wgt. % and phosphoric acid 1 wgt. % which resulted in a 4.88-log reduction in a 6.87-log $E.$ $coli$ inoculum. In contrast, Table 5 shows that 180 minute treatment of spinach with the combination "a2" that contained bromine 0.08 wgt. %, phosphoric acid 1 wgt. % and propylene glycol 2 wgt. % resulted in a 6.49-log reduction in a 6.57-log $E.$ $coli$ inoculum.

In yet another example, Table 3B shows that 180 minute treatment of spinach with each of hypochlorous acid 0.01 wgt. %, bromine 0.05 wgt. %, phosphoric acid 1 wgt. %, and propylene glycol 2 wgt. % alone in water caused a 5.01-log, 4.44-log, 4.13-log and 3.98-log reduction, respectively, in a 6.87-log $E.$ $coli$ inoculum. Table 4 shows similarly low antimicrobial activity by a combination of two components of bromine 0.08 wgt. % and phosphoric acid 1 wgt. % which resulted in a 4.88-log reduction in a 6.87-log $E.$ $coli$ inoculum. In contrast, Table 5 shows that 180 minute treatment of spinach with the combination "a5" that contained hypochlorous acid 0.01 wgt. %, bromine 0.05 wgt. %, phosphoric acid 1 wgt. %, and propylene glycol 2 wgt. %, resulted in a 6.57-log reduction in a 6.57-log $E.$ $coli$ inoculum.

The invention's compositions showed very effective antimicrobial activity (Tables 5, 6, 8 and 9). For example, Table 6 shows the antimicrobial activity of the invention's compositions on bacterial, bacteriophage, viral, fungal and nematode microbes, using a wide variety of agricultural products (including leafy vegetables, fruiting and flowering vegetables, podded vegetables, bulb and stem vegetables, root and tuberous vegetables, Rosaceae family fruits, Bramble fruits, berries, Asian fruit, North America fruit, raw meat, raw poultry, raw seafood, fresh seeds, edible sprouts, and nuts, eggs, fresh herbs, dried herbs, spices, animal hides, feathers) and inanimate objects (such as those encountered in hospitals, food processing plants, residential buildings, office buildings, etc.). Tables 3-5 and 6 also show that the invention's compositions produced at least a 3-log reduction in microbial inoculums that contained microbes ranging from 3-log to 8.78-log, after treatment for 2 minutes or longer at a temperature of at least 34° F. In addition, Tables 5 and 8 show 100% reduction in $E.$ $coli$ on spinach and strawberry after 180-minute treatment at about 33° F. with several of the invention's compositions. Additional exemplary compositions of the invention in Table 6 show 100% reduction in microbes when treating inanimate objects.

One surprising property of the invention's compositions is that they retain their antimicrobial activity over a broad range of temperatures, including from the freezing temperature of the composition to the temperature of autoclaving (about 120° C.). Thus, the invention's compositions may be used as antimicrobials at temperatures from the freezing temperature of the composition to 20° C., to 34° C., to 40° C., to 60° C., to 80° C., to 100° C. and/or to 120° C. For example, Table 6 shows that contacting shrimp, that was contaminated with $E.$ $coli$, for 30 minutes with the invention's compositions that had previously been frozen into ice cubes (about 29° F.) resulted in a 6.5-log reduction in $E.$ $coli$ from 6.87-log.

Thus, the invention's compositions advantageously retain their antimicrobial (and other) activities at temperatures equal to or below room temperature. "Room temperature" and "ambient temperature" are used interchangeably to refer to 21 degrees celcius (° C.), equivalent to 70 degrees Fahrenheit (° F.). "Chilling temperature" refers to a temperature less than room temperature, i.e., less than 21° C. (equivalent to less than 70° F.), including, but are not limited to, temperatures from 30° F. to 69° F., from 34° F. to 45° F., from 34° F. to 69° F., from 40° F. to 42° F., 40° F. to 69° F. and from 50° F. to 69° F. Temperatures greater than room temperature include, but are not limited to, temperatures from 71° F. to 220° F., from 100° F. to 220° F. and from 150° F. to 220° F. Thus, the invention's compositions are particularly useful at 30° F. to 40° F., preferably at 34° F., which are the temperatures at which many food products are preferably maintained prior to human consumption, such as in the field, during transport from the field, and before, during and/or after processing for human consumption. For agricultural products that may be ingested raw, in several embodiments, compositions brought in contact with these products are preferably formulated to contain one or more GRAS listed component.

Thus, the invention's compositions may be applied to fresh produce and ornamental plants at refrigerated temperatures of about 34° F. In another embodiment, the invention's compositions may be used when frozen, such as ice cubes or crushed ice. The temperature at which the compositions of the invention freeze will vary depending on the type and concentration of components in the composition. The invention's compositions are also useful antimicrobials at room temperature. For example in strawberries and tomatoes, a reduction in slime and mold was observed over a two-week period of storage at 75° F. following washing with the invention's compositions.

The invention's compositions are also useful for reducing odor associated with microbial breakdown of organic material, e.g., food.

In addition, the invention's compositions surprisingly reduced discoloration (e.g., pinking and browning) of agricultural products. Thus, in addition to the compositions' preservative effects during a two-week storage at 40° F. on varieties of lettuce and cabbage, a reduction in pinking and browning was also observed when applying anti-discoloration effective amounts of the invention's compositions. An "anti-discoloration effective amount" of a compound refers to an amount of the compound that reduces the level of discoloration compared to the level in the absence of the compound.

"Discoloration" refers to a change in color and/or hue. For example, discoloration of agricultural products includes pinking and browning that are generally observed after cutting produce and/or during storage. "Pinking" refers to a de novo development and/or increase in pink, red and/or rust color and/or hue such as that observed after storage at the cut edges of lettuce, especially iceberg lettuce, cabbage, celery, and Bok Choy. "Browning" refers to de novo development and/or increase in brown, grey and/or green color and/or hue such as that observed after storage at the cut edges of lettuce, cabbage, celery, Bok Choy, potatoes, parsnips, avocado, apples, strawberries, spinach, as well as after storage of meat (such as hamburger), poultry and seafood.

The level of discoloration may be subjectively determined using known methods (Schwank, U.S. Pat. No. 5,087,467) as well as using blind tests as previously described for other attributes such as crispness, color, and appearance of freshness (Estrada, U.S. Pat. No. 5,599,571). For example, at 3, 6 and 14 days after treatment with the invention's compositions, the agricultural produce is rated as having excellent, good, fair or poor color in a blind test by four individuals, and is compared with produce that is treated under the same conditions with the exception of omission of the invention's composition.

The invention's compositions may be applied by routine methods for application of antimicrobial solutions such as immersing, dipping, spraying, fogging, aerosoling, washing and scrubbing. "Fogging" refers to production of liquid droplets of 0.2 μm, or smaller, diameter, e.g., by applying differential pressure to the liquid. "Aerosoling" refers to production of liquid droplets of greater than 0.2 μm diameter, e.g., by applying high pressure to the liquid.

For large scale processing of produce (e.g., fruits and vegetables), a suitable volume of a working solution of the invention's compositions may be contained in a tank or flume, having agitation. The produce is deposited into this vessel for a period sufficient to reduce microbial contamination. The treated produce is then removed and transported down the line for further processing. Final rinsing is not necessary as the amount of residue is very low or non-toxic (Table 9), thus processing may include a step that leaves only a very thin, adherent film on the product's surfaces. This film furnishes an extended period of antimicrobial activity without adversely altering the color, texture and/or odor of the product surfaces during an extended shelf life.

In addition to the tank or flume, other methods are available by which the invention's compositions and their concentrates may be brought to contact the target microorganisms on any surface, including, without limitation, closed pipes, low-pressure spray, high-pressure spray, fog, vaporization, sonic energy, aerosols, wiping, immersion, scrubbing, swabbing, mopping, brushing, and gels. Contacting the invention's compositions with target microorganisms on any surface may be accomplished at atmospheric pressure and/or under a vacuum, i.e., at a pressure less than atmospheric pressure.

The invention's compositions may also be used during the processing of meat and poultry as previously described (Andrews et al., U.S. Pat. No. 5,490,992; Shane et al, U.S. Patent Application US 2002/0134317) and further described herein. For example, live animals or poultry are completely contacted with one or more of the invention's dilute compositions using best practices method. The treatment time is determined by whether subsequent processing is desired with a wet animal or whether it should appear to be dry. Without rinsing after this application, the invention's composition exhibits residual activity and substantially reduces the total microbial load. After the slaughter step, an animal carcass may be contacted with a more concentrated composition of the invention, and most preferably one that contains a surfactant, whereas one or more of the invention's dilute compositions may be used in subsequent steps according to best practices. The cutting and trimming workstations ideally should be cleaned and completely contacted with one or more of the invention's concentrated compositions between each carcass. In the case of poultry, where cross contamination is highly possible due to common wash and chiller tanks, one or more of the invention's dilute compositions may be used in these tanks. The last drainage step may be performed without the need for rinsing and the carcasses can be packaged normally. The antimicrobial composition is still effective at the low chilling temperatures and very low amounts.

Seeds and grains used for raw sprouts and/or other ingestion purposes are normally difficult to treat without harm and deterioration. However, contacting these products with one or more of the invention's dilute compositions and drying without the need for rinsing can substantially improve the product quality and safety.

Additional exemplary uses of the invention's methods are described herein in the Examples and Table 7 for treating fruits and vegetables, raw eggs, poultry with and without feathers, poultry feathers, meat, hides, seeds and nuts, seafood, dried goods, inanimate objects, skin, reverse osmosis membranes, etc.

After contact with the invention's composition, the treated products may be rinsed. Alternatively, the treated products may be allowed to dry (e.g., at ambient or chilling temperatures) or dried by spinning, heating, toweling, etc., without rinsing. One advantage of the invention's compositions is that, after drying, they form a very thin film on the surface of the treated products. This film is edible because of its low toxicity to higher life forms, while continuing to exhibit antimicrobial activity, thus eliminating the need for rinsing off the invention's composition from the treated agricultural (or other) products.

The invention's compositions show antibacterial activity against a wide spectrum of microbes, including bacterial, viral, fungal and nematode microbes. For example, data herein (Tables 3-6 and 8) show the antimicrobial activity of the invention's exemplary compositions on *E. Coli* (ATCC 25922) and the highly pathogenic *E. coli* O157:H7 strain (ATCC 43888) and *Salmonella enterica* (ATCC 10708).

The invention's compositions also show antibacterial activity against Gram-positive bacteria. Data herein (Table 6) show the antimicrobial activity of the invention's exemplary compositions on *Staphylococcus aureus* (ATCC 25923) and to a lesser extent on *Lactobacillus* sp. (ATCC 55326).

In addition, the invention's compositions show antifungal activity. Data herein (Table 6) show the antimicrobial activity of the invention's exemplary compositions on the fungi *Aspergillus flavus* (ATCC 15517) and *Septoria lycopersici* (ATCC Q99324) and toxic mold *Stachybotrys chartarum* (ATCC 9182).

The invention's compositions also show antiviral activity. Data herein (Table 6) show the antimicrobial activity of the invention's exemplary compositions on rhinovirus (ATCC vr1110).

Moreover, the invention's compositions show antibacteriophage activity. Data herein (Table 6) show the antimicrobial activity of the invention's exemplary compositions on bacteriophage T4 (ATCC 35060-B4).

Furthermore, the invention's compositions show antinematode activity. Data herein (Table 6) show the antimicrobial activity of the invention's exemplary compositions on *Aphelenchoides fragariae* (ATCC 12974), which is a nematode that destroys plant crops, necessitating burning of crops to eradicate the nematode.

One of the surprising properties of the invention's compositions is that they show a differential antimicrobial activity on pathogenic and non-pathogenic microbes. For example, a differential antimicrobial effect was observed between Gram-positive pathogenic and non-pathogenic bacteria. In particular, Table 6 shows the surprising result that exemplary composition "x4" of the invention caused greater than a 4-log reduction in a 4.21-log inoculum of *Staphylococcus aureus* (ATCC 25923) while the exemplary composition "x3" caused less than 2-log reduction in a 8.78-log inoculum of *Lactobacillus* sp (ATCC 55326).

Also, a differential antimicrobial activity was observed between pathogenic Gram-negative bacteria and non-pathogenic Gram-positive bacteria. In particular, Table 6 shows the surprising result that exemplary compositions x1, x2, x4, x5, x7, x9, x10, x11, x12, x13 and x15 of the invention caused greater than a 6-log reduction in about 6.87-log inoculum of *E. coli* (ATCC 25922 or ATCC 43888) while the exemplary composition "x3" caused less than 2-log reduction in a 8.78-log inoculum of *Lactobacillus* sp (ATCC 55326). Similarly, Table 6 shows the surprising result that exemplary compositions x4, x7, x10 and x11 of the invention caused greater than 5-log reduction in a 5.45-log inoculum of *S. enterica* (ATCC 25922) while the exemplary composition x3 caused less than 2-log reduction in a 8.78-log inoculum of *Lactobacillus* sp (ATCC 55326).

Not only was the differential antimicrobial activity observed between pathogenic and non-pathogenic bacteria, but it was also observed between pathogenic bacteria and non-pathogenic bacteriophage. For example, Table 6 shows the surprising result that exemplary compositions "x1" of the invention caused greater than a 6.8-log reduction in a 6.88-log inoculum of *E. coli* (ATCC 25922) while the same exemplary composition "x1" caused less than 1-log reduction in a 8.78-log inoculum of bacteriophage T4 (ATCC 35060-B4).

Additional differential antimicrobial activity was observed between pathogenic and non-pathogenic viruses. For example, Table 6 shows the surprising result that exemplary compositions "x13" of the invention caused a 2.4-log 100% 2.4-log (i.e., 100%) reduction in a 2.4-log inoculum of pathogenic Rhinovirus (ATCC vr1110) while composition "x1" caused less than 1-log reduction in a 8.78-log inoculum of non-pathogenic bacteriophage T4 (ATCC 35060-B4).

The invention's compositions are useful as antimicrobials in applications to a variety of surfaces, including agricultural products and inanimate objects.

In one embodiment the agricultural product is a leafy vegetable, as exemplified by, but not limited to, Amaranth (*Amaranthus cruentus*), Beet greens (*Beta vulgaris* subsp. *vulgaris*), Bitterleaf (*Vernonia calvoana*), Bok choy (*Brassica rapa* Chinensis group), Brussels sprout (*Brassica oleracea* Gemmifera group), Cabbage (*Brassica oleracea* Capitata group), Ceylon spinach (*Basella alba*), Chicory (*Cichorium intybus*), Chrysanthemum leaves (*Chrysanthemum coronarium*), Corn salad (*Valerianella locusta*), Cress (*Lepidium sativum*), Dandelion (*Taraxacum officinale*), Lettuce (*Lactuca sativa*), Mizuna greens (*Brassica rapa* Nipposinica group), Mustard (*Sinapis alba*), Napa/Chinese Cabbage (*Brassica rapa* Pekinensis group), New Zealand Spinach (*Tetragonia tetragonioides*), Orache (*Atriplex hortensis*), Pea sprouts/leaves (*Pisum sativum*), Sea beet (*Beta vulgaris* subsp. *maritima*), Seakale (*Crambe maritima*), Soko (*Celosia argentea*), Spinach (*Spinacia oleracea*), Swiss chard (*Beta vulgaris* subsp. *cicla* var. *flavescens*), Turnip greens (*Brassica rapa* Rapifera group), Watercress (*Nasturtium officinale*), Water spinach (*Ipomoea aquatica*), and Yau choy (*Brassica napus*).

In another embodiment, the agricultural product is a fruiting and/or flowering vegetable, as exemplified by, but not limited to, Armenian cucumber (*Cucumis melo* Flexuosus group), Eggplant or Aubergine (*Solanum melongena*), Avocado (*Persea americana*), Bell pepper (*Capsicum annuum*), Bitter melon (*Momordica charantia*), Cayenne pepper (*Capsicum frutescens*), Chayote (*Sechium edule*), Chili pepper (*Capsicum annuum* Longum group), Cucumber (*Cucumis sativus*), Globe Artichoke (*Cynara scolymus*), Perennial cucumber (*Coccinia grandis*), Pumpkin (*Cucurbita maxima, Cucurbita pepo*), Pattypan squash, Squash (aka marrow) (*Cucurbita pepo*), Corn (*Zea mays*), Sweet pepper (*Capsicum annuum* Grossum group), Tomato (*Solanum lycopersicum*), Tomatillo (*Physalis philadelphica*), Winter melon (*Benincasa hispida*), and Zucchini or Courgette (*Cucurbita pepo*).

In a further embodiment, the agricultural product is a podded vegetable, as exemplified by, but not limited to, American groundnut (*Apios americana*), Azuki bean (*Vigna angularis*), Black-eyed pea (*Vigna unguiculata* subsp. *unguiculata*), Chickpea (*Cicer arietinum*), Fava bean (*Vicia faba*), Indian pea (*Lathyrus sativus*), Lentil (*Lens culinaris*), Mung bean sprouts (*Vigna radiata*), Okra (*Abelmoschus esculentus*), Pea (*Pisum sativum*), Peanut (*Arachis hypogaea*), Pigeon pea (*Cajanus cajan*), Rice bean (*Vigna umbellatta*), Soybean (*Glycine max*), Winged bean (*Psophocarpus tetragonolobus*), and Yardlong bean (*Vigna unguiculata* subsp. *sesquipedalis*).

In yet another embodiment, the agricultural product is a bulb vegetable and/or stem vegetable, as exemplified by, but not limited to, Asparagus (*Asparagus officinalis*), Celery (*Apium graveolens*), Elephant Garlic (*Allium ampeloprasum* var. *ampeloprasum*), Florence fennel (*Foeniculum vulgare* var. *dulce*), Garlic (*Allium sativum*), Kohlrabi (*Brassica oleracea* Gongylodes group), Leek (*Allium porrum*), Onion (*Allium cepa*), Prussian asparagus (*Ornithogalum pyrenaicum*), Shallot (*Allium cepa* Aggregatum group), Welsh onion (*Allium fistulosum*), and Wild leek (*Allium tricoccum*).

In a further embodiment, the agricultural product is a root vegetable and/or tuberous vegetable, as exemplified by, but not limited to, Bamboo shoot, Beetroot (*Beta vulgaris* subsp. *vulgaris*), Black cumin (*Bunium persicum*), Broadleaf arrowhead (*Sagittaria latifolia*), Carrot (*Daucus carota*), Cassava (*Manihot esculenta*), Chinese artichoke (*Stachys affinis*), Daikon (*Raphanus sativus* Longipinnatus group), Earthnut pea (*Lathyrus tuberosus*), Ginger (*Zingiber officinale*), Hamburg parsley (*Petroselinum crispum* var. *tuberosum*), Jerusalem artichoke (*Helianthus tuberosus*), Jicama (*Pachyrhizus erosus*), Parsnip (*Pastinaca sativa*), Potato (*Solanum tuberosum*), Prairie turnip (*Psoralea esculenta*), Radish (*Raphanus sativus*), Rutabaga (*Brassica napus* Napobrassica group), Sweet Potato (Kumara), Taro (*Colocasia esculenta*), Turnip (*Brassica rapa* Rapifera group), Wasabi (*Wasabia japonica*), Water chestnut (*Eleocharis dulcis*), and Yam (*Dioscorea* spp.).

In another embodiment, the agricultural product is a sea vegetable, as exemplified by, but not limited to, Dabberlocks or badderlocks (*Alaria esculenta*), Dulse (*Palmaria palmata*), Hijiki (*Hizikia fusiformis*), Kombu (*Laminaria japonica*), Mozuku (*Cladosiphon okamuranus*), Sea grape (*Caulerpa* spp.), and Sea lettuce (*Ulva lactuca*).

In other embodiments, the agricultural product is a member of the Rosaceae family, as exemplified by, but not limited to, Apple and crabapple (*Malus*), Hawthorn (Crataegus and Rhaphiolepis), Loquat (*Eryobotrya japonica*), Pear, European and Asian species (*Pyrus*), Quince (*Cydonia oblonga* and *Chaenomeles*), Apricot (*Prunus armeniaca* or *Armeniaca vulgaris*), Cherry (*Prunus avium*), Peach (*Persica, vulgaris*), Plum (*Prunus salicina*), and Strawberry (*Fragaria ananassa*)

In another embodiment, the agricultural product is a bramble fruit, as exemplified by, but not limited to, Blackberry (genus *Rubus*) and Raspberry (genus *Rubus*), or is a berry, as exemplified by, but not limited to, Bilberry or whortleberry (*Vaccinium* spp.), Blueberry (*Vaccinium* spp.), Cranberry (*Vaccinium* spp.), Huckleberry (*Vaccinium* spp.), Barberry (*Berberis*; Berberidaceae), Currant (*Ribes* spp.; Grossulariaceae) including red, black, and white types, Elderberry (*Sambucus*; Caprifoliaceae), Gooseberry (*Ribes* spp.; Grossulariaceae), Hackberry (*Celtis* spp.; Cannabaceae), Honeysuckle, (*Lonicera* spp.; Caprifoliaceae), and Mulberry (*Morus* spp.; Moraceae).

In a further embodiment, the agricultural product is an Asian fruit, as exemplified by, but not limited to, Coconut (*Cocos* spp.; Arecaceae), Kiwifruit or Chinese gooseberry (*Actinidia* spp.; Actinidiaceae), Persimmon (aka Sharon Fruit) (*Diospyros kaki*; Ebenaceae), Rhubarb (Rheum rhaponticum; Polygonaceae), and Pineapple (*Ananas comosus*).

In another embodiment, the agricultural product is a North American fruit, as exemplified by, but not limited to, American grape, (*Vitis labrusca*; Vitaceae), American persimmon (*Diospyros virginiana*; Ebenaceae), Beach Plum (*Prunus maritima*; Rosaceae), Blueberry (*Vaccinium*, sect. *Cyanococcus*; Ericaceae), Persimmon (*Diospyros virginiana*; Ebenaceae), and Saw Palmetto (*Serenoa repens*; Ericaceae).

In yet another embodiment, the agricultural product is a citrus fruit, as exemplified by, but not limited to, Blood Orange, Citron (*Citrus medica*), Clementine (*Citrus reticulata* var. *Clementine*), Grapefruit (*Citrus paradisi*), Kumquat (*Fortunella*), Lemon (*Citrus limon*), Key Lime (*Citrus aurantifolia*), Mandarin (*Citrus reticulata*), Orange, (*Citrus sinensis*), Pomelo (also known as the shaddock) (*Citrus maxima*), and Sweet Lemon (*Citrus limetta*).

In further embodiments, the agricultural product is meat, such as raw and/or cooked beef, pork, and lamb, exemplified by beef steak, beef hamburger, pork chop, pork sausage, lamb shank, and bacon.

In other embodiments, the agricultural product is poultry, such as raw and/or cooked turkey, chicken, and duck, including whole poultry and poultry parts, e.g., breast, thigh, drumstick, and poultry products e.g., poultry eggs, and egg shells.

In yet other embodiments, the agricultural product is seafood such as raw (e.g., sushi) and/or cooked fish (e.g., salmon, bass, tuna), including whole fish and fish parts, e.g., steak, fillet, as well as shellfish (e.g., mussels, clams, oysters, and shrimp).

In further embodiments, the agricultural product is a fresh or cooked seed or nut, as exemplified by, but not limited to, almonds (*Prunus communis*), walnuts (*Juglans nigra*), sunflower (*Helianthus, annuus*), and pumpkin (*Cucurbita pepo*).

Other embodiments of agricultural products include fresh and/or dried herb such as parsley (*Carum petroselinum*), cumin (*Cuminum cyminum*), sweet basil (*Ocimum basilicum*), rosemary (*Rosmarinus officinalis*), and mint (*Mentha* spp).

Further embodiments of agricultural product include animal hide (e.g., cow hide and pig hide), and poultry feathers (e.g., chicken feathers, turkey feathers and goose feathers).

Other surfaces that may be treated with the invention's compositions include skin (e.g., human skin, cow udders, cow teats, etc.) and inanimate objects (e.g., door handles, door knobs, door frames, table surfaces, stair railings).

EXPERIMENTAL

The following examples serve to illustrate certain preferred embodiments and aspects of the present invention and are not to be construed as limiting the scope thereof.

Example 1

Synergistic Antimicrobial Activity

This example provides the results for antimicrobial activity of components of exemplary invention's compositions when the components were used alone (Tables 3A and 3B), or as a combination of two components (Tables 3A and 4), or of at least three components (Tables 3A and 5).

Produce was rinsed with sterile water before refrigerating. Produce was dip-inoculated and let stand for 24 hrs prior to component testing. 25-gram samples were pureed with 475 grams of sterile water (20 fold dilution). Pureed samples were spread-plated on pre-made Mac Conkey with mug agar plates #221172 from Becton, Dickinson Biosciences and incubated at about 44° F. for 24-30 hours. Colonies were counted using colony counter Bantex 920A with UV light 366 nM. The results are shown in Table 3A.

TABLE 3A

Antimicrobial activity (log reduction) of components used singly, in combination of two components, in combination of three components, and in combination of four components.

| | *E. Coli* (ATCC 29522) inoculum 5.45 log | | | | | |
|---|---|---|---|---|---|---|
| | Strawberry 25 grams | | | Spinach leaf 25 grams | | |
| Component[a] | 2 min.[b] | 30 min.[b] | 180 min.[b] | 2 min.[b] | 30 min.[b] | 180 min.[b] |
| Single Components | | | | | | |
| Propylene Glycol (0.03 wgt. %) | 1.83 | 2.24 | 2.55 | 1.71 | 2.1 | 2.4 |
| Phosphoric Acid (0.3 wgt. %) | 2.15 | 2.17 | 2.62 | 2.00 | 2.1 | 2.55 |
| Hydrogen Peroxide (0.2 wgt. %) | 2.0 | 2.66 | 2.99 | 1.8 | 2.44 | 2.77 |
| Sodium Lauryl Sulfate (0.0005 wgt. %) | 1.2 | 1.5 | 1.89 | 1.0 | 1.6 | 1.78 |

TABLE 3A-continued

Antimicrobial activity (log reduction) of components used singly, in combination of two components, in combination of three components, and in combination of four components.

| | E. Coli (ATCC 29522) inoculum 5.45 log | | | | | |
|---|---|---|---|---|---|---|
| | Strawberry 25 grams | | | Spinach leaf 25 grams | | |
| Component[a] | 2 min.[b] | 30 min.[b] | 180 min.[b] | 2 min.[b] | 30 min.[b] | 180 min.[b] |
| Potable Water alone (33° F., 100 wgt. %) | 0.91 | 0.98 | 1.05 | 0.78 | 0.82 | 0.88 |
| Two Components | | | | | | |
| Propylene Glycol (0.03 wgt. %) and Phosphoric Acid (0.3 wgt. %) | 2.99 | 4.01 | 5.45 | 2.78 | 3.89 | 5.45 |
| Three Components | | | | | | |
| Propylene Glycol (0.03 wgt. %) and Phosphoric Acid (0.3 wgt. %) and Hydrogen Peroxide (0.2 wgt. %) | 3.34 | 4.45 | 5.45 | 3.12 | 4.12 | 5.45 |
| Four Components | | | | | | |
| Propylene Glycol (0.03 wgt. %) and Phosphoric Acid (0.3 wgt. %) and Hydrogen Peroxide (0.2 wgt. %) and Sodium Lauryl Sulfate (0.0005 wgt. %)[c] | 4.12 | 5.11 | 5.45 | 3.98 | 4.99 | 5.45 |

[a] Component was dissolved in potable water to make a total of 100 g. The component and sterile water were chilled to 34° F.
[b] Fruit and vegetable were chilled to 40° F. and washed in the solution containing the listed component for the period indicated. Testing was done at ambient temperature of about 68° F.
[c] The solution containing Propylene Glycol 0.03 wgt. %, ortho-Phosphoric Acid 0.3 wgt. %, Hydrogen Peroxide 0.2 wgt. % and Sodium Lauryl Sulfate 0.0005 wgt. % is an exemplary composition of solution D of Table 1. It was made by using a concentrated solution of Propylene Glycol 3 wgt. %, ortho-Phosphoric Acid 30 wgt. %, Hydrogen Peroxide 20 wgt. % and Sodium Lauryl Sulfate 0.05 wgt. % diluted 100 to 1.

TABLE 3B

Antimicrobial activity (log reduction) of single components

| | E. Coli (ATCC 43888) inoculum 6.87-log | | | | | |
|---|---|---|---|---|---|---|
| | Strawberry 25 grams | | | Spinach leaf 25 grams | | |
| Component[a] | 2 min.[b] | 30 min.[b] | 180 min.[b] | 2 min.[b] | 30 min.[b] | 180 min.[b] |
| Propylene Glycol (2 wgt. %) | 2.23 | 2.69 | 4.47 | 2.40 | 2.54 | 3.98 |
| Acetic Acid (1 wgt. %) | 2.52 | 2.73 | 4.45 | 2.5 | 2.61 | 4.01 |
| Citric Acid (1 wgt. %) | 2.25 | 2.68 | 4.43 | 2.11 | 2.34 | 4.09 |
| Phosphoric Acid (1 wgt. %) | 2.58 | 2.87 | 4.22 | 2.5 | 2.71 | 4.13 |
| Hypochlorous Acid (0.01 wgt. %) | 2.45 | 3.45 | 5.69 | 2.32 | 3.4 | 5.01 |
| Bromine (0.08 wgt. %) | 2.32 | 3.32 | 4.89 | 2.11 | 3.28 | 4.44 |
| Hydrogen Peroxide (2 wgt. %) | 2.11 | 2.69 | 4.65 | 2.01 | 2.6 | 3.89 |
| Ozone (0.001 wgt. %) | 2.89 | 3.12 | 4.12 | 2.34 | 2.58 | 3.63 |
| Sodium Lauryl Sulfate (0.5 wgt. %) (CAS 009004-82-4) | 1.89 | 2.69 | 3.56 | 1.77 | 2.29 | 3.26 |
| Octyl Phenol Ethoxylate (0.5 wgt. %) | 1.05 | 2.78 | 3.9 | 1.15 | 2.47 | 3.11 |
| Potable Water alone | 0.98 | 1.04 | 1.2 | 0.68 | 1 | 1.1 |

[a] Component was dissolved in potable water to make a total of 100 g and tested at about 33° F.
[b] Fruit and vegetable were washed in the solution containing the listed component for the period indicated.

TABLE 4

Antimicrobial activity (log reduction) of a combination of two components

| | E. Coli (ATCC 43888) inoculum 6.87-log | | | | | |
|---|---|---|---|---|---|---|
| | Strawberry 25 grams | | | Spinach leaf 25 grams | | |
| Component[a] | 2 min.[b] | 30 min.[b] | 180 min.[b] | 2 min.[b] | 30 min.[b] | 180 min.[b] |
| Hypochlorous Acid 0.01 wgt. % & Acetic Acid 1 wgt. % | 2.68 | 3.74 | 4.98 | 2.48 | 3.54 | 4.78 |
| Hypochlorous Acid 0.01 wgt. % & Citric Acid 1 wgt. % | 2.55 | 3.51 | 4.66 | 2.25 | 3.3 | 4.48 |
| Hypochlorous Acid 0.01 wgt. % & Phosphoric Acid 1 wgt. % | 2.81 | 3.94 | 5.13 | 2.61 | 3.74 | 4.9 |
| Bromine 0.08 wgt. % & Acetic Acid 1 wgt. % | 2.71 | 3.39 | 4.91 | 2.51 | 3.1 | 4.7 |
| Bromine 0.08 wgt. % & Citric Acid 1 wgt. % | 2.44 | 3.64 | 4.71 | 2.52 | 3.54 | 4.71 |
| Bromine 0.08 wgt. % & Phosphoric Acid 1 wgt. % | 2.82 | 3.93 | 4.74 | 2.42 | 3.63 | 4.88 |
| Hydrogen Peroxide 2 wgt. % & Acetic Acid 1 wgt. % | 2.51 | 3.56 | 4.89 | 2.43 | 3.5 | 4.77 |
| Hydrogen Peroxide 2 wgt. % & Citric Acid 1 wgt. % | 2.54 | 3.57 | 4.85 | 2.4 | 3.68 | 4.85 |
| Hydrogen Peroxide 2 wgt. % & Phosphoric Acid 1 wgt. % | 2.72 | 3.81 | 4.99 | 2.69 | 3.71 | 4.99 |
| Ozone 0.001 wgt. % & Acetic Acid 1 wgt. % | 2.49 | 3.79 | 4.96 | 2.65 | 3.5 | 4.9 |
| Ozone 0.001 wgt. % & Citric Acid 1 wgt. % | 2.48 | 3.77 | 4.96 | 2.48 | 3.57 | 4.7 |
| Ozone 0.001 wgt. % & Phosphoric Acid 1 wgt. % | 2.47 | 3.78 | 4.97 | 2.5 | 3.7 | 4.78 |
| Hypochlorous Acid 0.01 wgt. % & Sodium Lauryl Sulfate 0.5 wgt. % | 2.41 | 3.31 | 4 | 2.61 | 3.41 | 4.1 |
| Hypochlorous Acid 0.01 wgt. % & Octyl Phenol Ethoxylate 0.5 wgt. % | 2.56 | 3.41 | 4.11 | 2.4 | 3.21 | 4 |
| Bromine 0.08 wgt. % & Sodium Lauryl Sulfate 0.5 wgt. % | 2.31 | 2.98 | 3.98 | 2.3 | 2.88 | 3.99 |
| Bromine 0.08 wgt. % & Octyl Phenol Ethoxylate 0.5 wgt. % | 2.45 | 2.99 | 4 | 2.4 | 2.9 | 3.78 |
| Hydrogen Peroxide 2 wgt. % & Sodium Lauryl Sulfate 0.5 wgt. % | 2.34 | 2.89 | 3.57 | 2.35 | 2.88 | 3.55 |
| Hydrogen Peroxide 2 wgt. % & Octyl Phenol Ethoxylate 0.5 wgt. % | 2.46 | 2.93 | 3.91 | 2.33 | 2.78 | 3.81 |
| Ozone 0.001 wgt. % & Sodium Lauryl Sulfate 0.5 wgt. % | 2.56 | 3.51 | 3.98 | 2.56 | 3.31 | 3.78 |
| Ozone 0.001 wgt. % & Octyl Phenol Ethoxylate 0.5 wgt. % | 2.54 | 3.41 | 3.9 | 2.45 | 3.22 | 3.39 |

[a]Component was dissolved in potable water to make a total of 100 g and tested at about 33° F.
[b]Fruit and vegetable were washed in the solution containing the listed component for the period indicated.

TABLE 5

Antimicrobial activity (log reduction) of a combination of at least three components.

| | E. Coli (ATCC 43888) inoculum 6.57-log | | | | | |
|---|---|---|---|---|---|---|
| | Strawberry 25 grams | | | Spinach leaf 25 grams | | |
| Component[a] | 2 min.[b] | 30 min.[b] | 180 min.[b] | 2 min.[b] | 30 min.[b] | 180 min.[b] |
| (a1) Hypochlorous Acid 0.01 wgt. % & Phosphoric Acid 1 wgt. % & Propylene Glycol 2 wgt. % | 4 | 5.1 | 6.57 | 4.5 | 5.2 | 6.57 |
| (a2) Bromine 0.08 wgt. % & Phosphoric Acid 1 wgt. % & Propylene Glycol 2 wgt. % | 3.9 | 4.48 | 6.49 | 4 | 4.58 | 6.49 |

TABLE 5-continued

Antimicrobial activity (log reduction) of a combination of at least three components.

E. Coli (ATCC 43888) inoculum 6.57-log

| | Strawberry 25 grams | | | Spinach leaf 25 grams | | |
|---|---|---|---|---|---|---|
| Component[a] | 2 min.[b] | 30 min.[b] | 180 min.[b] | 2 min.[b] | 30 min.[b] | 180 min.[b] |
| (a3) Hydrogen Peroxide 2 wgt. % & Phosphoric Acid 1 wgt. % & Propylene Glycol 2 wgt. % | 3.98 | 4.22 | 6.5 | 3.99 | 4.32 | 6.5 |
| (a4) Ozone 0.001 wgt. % & Phosphoric Acid 1 wgt. % & Propylene Glycol 2 wgt. % | 3.99 | 4.77 | 6.49 | 3.99 | 4.76 | 6.48 |
| (a5) Hypochlorous Acid 0.01 wgt. % & Bromine 0.05 wgt. % & Phosphoric Acid 1 wgt. % & Propylene Glycol 2 wgt. % | 4.12 | 5.44 | 6.57 | 4.22 | 5.3 | 6.57 |

[a]Components were dissolved in potable water to make a total of 100 g and tested at about 33° F.
[b]Fruit and vegetable were washed in the solution containing the listed components for the period indicated.

In the above Tables 3-5, the antimicrobial activity is reported as a log reduction which was determined by calculating the difference between the $\log_{10}$ of the initial inoculum count and the $\log_{10}$ of the inoculum's count after exposure to the listed components for about 2 minutes, about 30 minutes, or about 180 minutes, at about 33° F.

To determine bacterial kill-rate or $\log_{10}$ reduction, a 0.1 ml aliquot of a bacterial culture suspension incubated for about 24 hours in tryptic soy broth having an initial inoculum count of between about $10^6$ to about $10^8$ cells/ml was added to a test sample of either fruits (strawberry 25 grams) or vegetables (spinach 25 grams) at about 33° F. In this example, culture suspensions were prepared from E. coli (ATCC 43888). After about two minutes, thirty minutes or one hundred eighty minutes of this treatment, using the USDA recommended procedure, the inoculated material was placed into a 225 ml solution of EC Medium, with mug, in a stomacher bag and thoroughly mixed for a minimum of two minutes and incubated at 35° C. for twenty four hours. Next, the cultures were diluted 10-fold in Butterfield's Phosphate Diluent and 0.1 ml of the dilutions were inoculated using the spread plate technique onto MacConkey Sorbitol Agar (MSA). Then the plates were incubated for twenty four hours at 42° C. Plates were then removed and examined for the number of colonies.

The data demonstrate synergy of the invention's components. For example, Table 3B shows that 180 minute treatment of spinach with each of hypochlorous acid 0.01 wgt. %, phosphoric acid 1 wgt. % and propylene glycol 2 wgt. % alone in water caused a 5.01-log, 4.13-log, and 3.98-log reduction, respectively, in a 6.87-log E. coli inoculum. Table 4 shows similarly low antimicrobial activity by a combination of two components of hypochlorous acid 0.01 wgt. % and phosphoric acid 1 wgt. % which resulted in a 4.9-log reduction in a 6.87-log E. coli inoculum. In contrast, Table 5 shows that 180 minute treatment of spinach with the combination "a1" that contained hypochlorous acid 0.01 wgt. %, phosphoric acid 1 wgt. %, and propylene glycol 2 wgt. % resulted in a 100% reduction in a 6.57-log E. coli inoculum.

Similarly, Table 3B shows that 180 minute treatment of spinach with each of bromine 0.08 wgt. %, phosphoric acid 1 wgt. % and propylene glycol 2 wgt. % alone caused a 4.44-log, 4.13-log, and 3.98-log reduction, respectively, in a 6.87-log E. coli inoculum. Table 4 shows similarly low antimicrobial activity by a combination of two components of bromine 0.08 wgt. % and phosphoric acid 1 wgt. % which resulted in a 4.88-log reduction in a 6.87-log E. coli inoculum. In contrast, Table 5 shows that 180 minute treatment of spinach with the combination "a2" that contained bromine 0.08 wgt. %, phosphoric acid 1 wgt. % and propylene glycol 2 wgt. % resulted in a 6.49-log reduction in a 6.57-log E. coli inoculum.

In yet another example, Table 3B shows that 180 minute treatment of spinach with each of hypochlorous acid 0.01 wgt. %, bromine 0.05 wgt. %, phosphoric acid 1 wgt. %, and propylene glycol 2 wgt. % alone caused a 5.01-log, 4.44-log, 4.13-log and 3.98-log reduction, respectively, in a 6.87-log E. coli inoculum. Table 4 shows similarly low antimicrobial activity by a combination of two components of bromine 0.08 wgt. % and phosphoric acid 1 wgt. % which resulted in a 4.88-log reduction in a 6.87-log E. coli inoculum. In contrast, Table 5 shows that 180 minute treatment of spinach with the combination "a5" that contained hypochlorous acid 0.01 wgt. %, bromine 0.05 wgt. %, phosphoric acid 1 wgt. %, and propylene glycol 2 wgt. % resulted in a 100% reduction in a 6.57-log E. coli inoculum.

Example 2

Antimicrobial Activity Using Agricultural Products and Inanimate Objects

This example shows the results of treating a variety of agricultural products, skin, and inanimate objects with the invention's exemplary compositions "x1" to "x15" that are described above in Table 2.

TABLE 6

Antimicrobial Activity Of Exemplary Compositions Of The Invention

| Material | Reference Number of Exemplary Composition | Treatment Method[a] (see Table 7 for details) | Microbe Tested[b] | Log Microbe Inoculum | Log Reduction in Microbe[c] | Notes |
|---|---|---|---|---|---|---|
| Botanical Leafy vegetables | | | | | | |
| Bok choy (*Brassica rapa Chinensis* group) | x1 | t1 | b2 (*E. coli* generic) | 6.88 | >6.7 | |
| | x3 | t3 | b4 (*Lactobacillus* sp.) | 8.78 | <2.3 | Composition x3 diluted 100 to 1 |
| Cabbage (*Brassica oleracea Capitata* group) | x1 | t1 | b2 (*E. coli* generic) | 6.88 | >6.8 | |
| | x3 | t3 | b4 (*Lactobacillus* sp.) | 8.78 | <1 | Composition x3 diluted 100 to 1 |
| | x15 | t2 | b1 (*E. coli*) | 6.87 | >6.7 | Composition x15 diluted 10 to 1 |
| Dandelion (*Taraxacum officinale*) | x1 | t1 | b2 (*E. coli* generic) | 6.88 | >6.8 | |
| | x3 | t3 | b4 (*Lactobacillus* sp.) | 8.78 | <2 | Composition x3 diluted 100 to 1 |
| Lettuce (*Lactuca sativa*) | x1 | t1 | b2 (*E. coli* generic) | 6.88 | >6.8 | |
| | x3 | t3 | b4 (*Lactobacillus* sp.) | 8.78 | <3 | Composition x3 diluted 100 to 1 |
| | x4 | t2 | b3 (*Staphylococcus aureus*) | 4.21 | >4 | |
| | x4 | t2 | b5 (*Salmonella enteric*) | 5.54 | >5 | |
| Mustard (*Sinapis alba*) | x1 | t1 | b2 (*E. coli* generic) | 6.88 | >6.8 | |
| | x3 | t3 | b4 (*Lactobacillus* sp.) | 8.78 | <1 | Composition x3 diluted 100 to 1 |
| Napa/Chinese Cabbage (*Brassica rapa Pekinensis* group) | x1 | t1 | b2 (*E. coli* generic) | 6.88 | >6.6 | |
| | x3 | t3 | b4 (*Lactobacillus* sp.) | 8.78 | <1 | Composition x3 diluted 100 to 1 |
| Spinach (*Spinacia oleracea*) | x1, | t1 | b2 (*E. coli* generic) | 6.88 | >6.7 | |
| | x3 | t3 | b4 (*Lactobacillus* sp.) | 8.78 | <2 | Composition x3 diluted 100 to 1 |
| | x11 | t3 | b1 (*E. coli*) | 6.87 | >6.5 | Composition x11 diluted 200 to 1 |
| | x7 | t2 | b5 (*Salmonella enterica*) | 5.45 | >5 | |
| Swiss chard (*Beta vulgaris* subsp. *cicla* var. *flavescens*) | x1 | t1 | b2 (*E. coli* generic) | 6.88 | >6.8 | |
| | x3 | t3 | b4 (*Lactobacillus* sp.) | 8.78 | <1 | Composition x3 diluted 100 to 1 |
| | x9 | t1 | b2 (*E. coli* generic) | 6.88 | >6.6 | |
| | x1 | t1 | p1 (bacteriophage T4) | 3.1 | <1 | |

TABLE 6-continued

Antimicrobial Activity Of Exemplary Compositions Of The Invention

| Material | Reference Number of Exemplary Composition | Treatment Method[a] (see Table 7 for details) | Microbe Tested[b] | Log Microbe Inoculum | Log Reduction in Microbe[c] | Notes |
|---|---|---|---|---|---|---|
| Botanical Fruiting and flowering vegetables | | | | | | |
| Avocado (*Persea americana*) | x1 | t3 | b1 (*E. coli*) | 6.87 | >6.7 | |
|  | x2 | t1 | b1 (*E. coli*) | 6.87 | >6 | |
| Bell pepper (*Capsicum annuum*) | x4 | t3 | b1 (*E. coli*) | 6.87 | >6.8 | Composition x4 diluted 100 to 1 |
|  | x9 | t1 | b1 (*E. coli*) | 6.87 | >6.7 | |
| Globe Artichoke (*Cynara scolymus*) | x5 | t3 | b1 (*E. coli*) | 6.87 | >6.6 | |
|  | x7 | t2 | b1 (*E. coli*) | 6.87 | >6.8 | |
| Tomato (*Solanum lycopersicum*) | x1 | t1 | b2 (*E. coli* generic) | 6.88 | >6.8 | |
|  | x2 | t2 | b5 (*Salmonella enterica*) | 5.45 | <2 | |
|  | x11 | t3 | m1 (*Stachybotrys chartarum*) | 5.5 | >4 | Composition x11 diluted 100 to 1 |
|  | x1 | t2 | b2 (*E. coli* generic) | 6.88 | >6.6 | |
|  | x13 | t3 | m1 (*Stachybotrys chartarum*) | 5.5 | >5 | Composition x13 diluted 100 to 1 |
| Botanical Podded vegetables | | | | | | |
| Mung bean sprouts (*Vigna radiata*) | x1 | t1 | b1 (*E. coli*) | 6.87 | >6.5 | |
|  | x4 | t3 | b1 (*E. coli*) | 6.87 | >6.1 | Composition x4 diluted 100 to 1 |
| Botanical Bulb and stem vegetables | | | | | | |
| *Asparagus* (*Asparagus officinalis*) | x10 | t3 | b1 (*E. coli*) | 6.87 | >6.5 | |
| Botanical Root and tuberous vegetables | | | | | | |
| Carrot (*Daucus carota*) | x10 | t3 | b1 (*E. coli*) | 6.87 | >6.6 | |
| Botanical Rosaceae family | | | | | | |
| Apple and crabapple (*Malus*) | x10 | t3 | b1 (*E. coli*) | 6.87 | >6.6 | |
| Peach (*Persica, vulgaris*) | x10 | t3 | b1 (*E. coli*) | 6.87 | >6.5 | |
| Strawberry (*Fragaria ananassa*) | x1 | t3 | b1 (*E. coli*) | 6.87 | >6.7 | |
|  | x4 | t1 | b2 (*E. coli* generic) | 6.88 | >6.6 | Composition x4 diluted 100 to 1 |
|  | x11 | t2 | m1 | 5.5 | >4 | Composition |

TABLE 6-continued

Antimicrobial Activity Of Exemplary Compositions Of The Invention

| Material | Reference Number of Exemplary Composition | Treatment Method[a] (see Table 7 for details) | Microbe Tested[b] | Log Microbe Inoculum | Log Reduction in Microbe[c] | Notes |
|---|---|---|---|---|---|---|
| Botanical Bramble fruits | | | (*Stachybotrys chartarum*) | | | x11 diluted 50 to 1 |
| Blackberry, (genus *Rubus*) | x11 | t3 | b1 (*E. coli*) | 6.87 | >6.8 | Composition x11 diluted 100 to 1 |
| Botanical Berries | | | | | | |
| Cranberry (*Vaccinium* spp.) | x11 | t3 | b1 (*E. coli*) | 6.87 | >6.7 | Composition x11 diluted 100 to 1 |
| Botanical Fruit Asian | | | | | | |
| Pineapple cut into slices (*Ananas comosus*) | x11 | t3 | b1 (*E. coli*) | 6.87 | >5 | Composition x11 diluted 500 to 1 |
| Botanical Fruit North American | | | | | | |
| Blueberry (*Vaccinium*, sect. *Cyanococcus*; *Ericaceae*) | x11 | t3 | b1 (*E. coli*) | 6.87 | >6 | Composition x11 diluted 100 to 1 |
| Meat Raw | | | | | | |
| Beef Hamburger | x1 | t8 | b1 (*E. coli*) | 6.87 | >5 | |
| Pork Chop | x11 | t9 | b1 (*E. coli*) | 6.87 | >6 | Composition x11 diluted 100 to 1 |
| Bacon | x1 | t8 | b1 (*E. coli*) | 6.87 | >6.5 | |
| Poultry Raw | | | | | | |
| Turkey breast | x11 | t6 | b1 (*E. coli*) | 6.87 | >6 | Composition x11 diluted 100 to 1 |
| Chicken breast | x1 | t6 | b1 (*E. coli*) | 6.87 | >6.8 | |
| Fish Raw | | | | | | |
| Salmon steak | x1 | t13 | b1 (*E. coli*) | 6.87 | >6.8 | |
| Bass steak | x12 | t13 | b1 (*E. coli*) | 6.87 | >6.8 | |
| tuna processed raw | x12 | t13 | b1 (*E. coli*) | 6.87 | >6 | |
| Shellfish | | | | | | |
| Clams raw | x1 | t14 | b1 (*E. coli*) | 6.87 | >6 | |
| shrimp raw not frozen | x1 | t14 | b1 (*E. coli*) | 6.87 | >6.5 | |
| Seeds and Nuts fresh (not dried) | | | | | | |
| Almonds (*Prunus communis*) | x12 | t11 | m1 (*Stachybotrys chartarum*) | 5.5 | >4 | |
| | x12 | t11 | f1 (*Aspergillus flavus*) | 2.3 | >1.8 | |

TABLE 6-continued

Antimicrobial Activity Of Exemplary Compositions Of The Invention

| Material | Reference Number of Exemplary Composition | Treatment Method[a] (see Table 7 for details) | Microbe Tested[b] | Log Microbe Inoculum | Log Reduction in Microbe[c] | Notes |
|---|---|---|---|---|---|---|
| Eggs (topical Shells) | | | | | | |
| Chicken fresh eggs | x15 | t4 | b1 (*E. coli*) | 6.87 | >6 | |
| Herbs fresh | | | | | | |
| parsley (*Carum petroselinum*) | x1 | t1 | b1 (*E. coli*) | 6.87 | >6 | |
| Herbs Dried | | | | | | |
| parsley (*Carum petroselinum*) | x13 | t15 | b1 (*E. coli*) | 6.87 | >6 | Composition x13 diluted 200 to 1 |
| Animal Hides | | | | | | |
| Cow Hide | x11 | t10 | b1 (*E. coli*) | 6.87 | >6 | Composition x11 diluted 50 to 1 |
| Animal feathers | | | | | | |
| Chicken feathers | x11 | t7 | b5 (*Salmonella enterica*) | 5.45 | >5 | |
| Human skin | | | | | | |
| Male age 46, forearm | x10 | t19 | skin test | | — | |
| Male age 78, top left hand | x10 | t19 | b3 (*Staphylococcus aureus*) | 4.21 | — | |
| Structures | | | | | | |
| Pine wood sanded 6" × 6" | x5 | t18 | m1 (*Stachybotrys chartarum*) | 5.5 | >3.5 | |
| | x9 | t18 | b1 (*E. coli*) | 6.87 | >5 | |
| | x14 | t18 | b2 (*E. coli* generic) | 6.88 | >5 | |
| Teflon sheet 6" × 6" | x5 | t18 | m1 (*Stachybotrys chartarum*) | 5.5 | >5 | |
| | x9 | t18 | b1 (*E. coli*) | 6.87 | >6 | |
| | x14 | t18 | b2 (*E. coli* generic) | 6.88 | >6 | |
| Ultra high molecular weight (UHMW) polyethylene sheet 6" × 6" | x5 | t18 | m1 (*Stachybotrys chartarum*) | 5.5 | >5 | |
| | x9 | t18 | b1 (*E. coli*) | 6.87 | >6 | |
| | x14 | t18 | b2 (*E. coli* generic) | 6.88 | >6 | |
| ceramic tile 3" × 3" | x13 | t17 | m1 (*Stachybotrys chartarum*) | 5.5 | 5.5 | Composition x13 diluted 10 to 1 |
| | x13 | t17 | v1 (Rhinovirus) | 2.4 | 2.4 | Composition x13 diluted 10 to 1 |
| stainless steel 6" × 6" | x13 | t17 | m1 (*Stachybotrys chartarum*) | 5.5 | 5.5 | Composition x13 diluted 10 to 1 |
| | x13 | t17 | v1 (Rhinovirus) | 2.4 | 2.4 | Composition x13 diluted 10 to 1 |
| cement block 6" × 6" | x13 | t17 | m1 (*Stachybotrys chartarum*) | 5.5 | 5.5 | Composition x13 diluted 10 to 1 |

TABLE 6-continued

Antimicrobial Activity Of Exemplary Compositions Of The Invention

| Material | Reference Number of Exemplary Composition | Treatment Method[a] (see Table 7 for details) | Microbe Tested[b] | Log Microbe Inoculum | Log Reduction in Microbe[c] | Notes |
|---|---|---|---|---|---|---|
| | x13 | t17 | v1 (Rhinovirus) | 2.4 | 2.4 | Composition x13 diluted 10 to 1 |
| Glass sheet 6" × 6" | x13 | t17 | m1 (Stachybotrys chartarum) | 5.5 | 5.5 | Composition x13 diluted 10 to 1 |
| | x13 | t17 | v1 (Rhinovirus) | 2.4 | 2.4 | Composition x13 diluted 10 to 1 |
| Painted (acrylic paint) wood 6" × 6" | x13 | t18 | m1 (Stachybotrys chartarum) | 5.5 | >4 | Composition x13 diluted 10 to 1 |
| | x13 | t18 | v1 (Rhinovirus) | 2.4 | >2 | Composition x13 diluted 10 to 1 |
| ICE with shrimp | x1 | t16 | b1 (E. coli) | 6.87 | >6 | |
| | x2 | t16 | b1 (E. coli) | 6.87 | >6.5 | |
| Plant specific | | | | | | |
| Tomato leaf (Solanum lycopersicum) | x11 | t1 | f2 (Septoria lycopersici) | 3.2 | >2 | Composition x11 diluted 50 to 1 |
| | x11 | t1 | n1 (Aphelenchoides fragariae) | 2.3 | >1.8 | Composition x11 diluted 50 to 1 |
| Poultry feathers | x10 | t7 | b5 (Salmonella enterica) | 5.45 | >5 | |
| Reverse Osmosis (RO) membrane | x3 | t21 | b2 (E. coli generic) | 6.88 | 6.88 | Composition x3 diluted 200 to 1 |

[a]All tests were performed according to FDA specifications.
[b]Microbes: E. coli (ATCC 43888), E. coli generic (ATCC 25922), Staphylococcus aureus (ATCC 25923), Salmonella enterica (ATCC 10708), Lactobacillus sp. (ATCC 55326). Aspergillus flavus (ATCC 15517) is an almond fungus; Septoria lycopersici (ATCC Q99324) is a tomato leaf fungus; Stachybotrys chartarum (ATCC 9182) is black mold (toxic); bacteriophage T4 (ATCC 35060-B4); Aphelenchoides fragariae (ATCC 12974) is a nematode that destroys plant crops, necessitating burning of crops to eradicate the nematode; rhinovirus (ATCC vr1110) causes head cold in humans.
[c]< means less than; > means more than.

TABLE 7

Exemplary Treatment Methods Used To Obtain Some Of The Data In Table 6

| Treatment Reference | Treatment Method[a] |
|---|---|
| t1 | Fruits and vegetables may be dipped, sprayed, fogged or aerosoled at temperatures equal to or above 40 degrees F. as a pretreatment before the final processing wash. Contact time with the invention's composition may be 45 minutes or longer. |
| t2 | Fruits and vegetables may be dipped, sprayed, fogged or aerosoled at temperatures equal to or below 40 degrees F. as a pretreatment before the final processing wash. Contact time with the invention's composition may be 100 minutes or longer. |
| t3 | Fruits and vegetables may be liquid conveyed in composition at temperatures equal to or below 40 degrees F. as a final processing wash. Contact time with the invention's composition may be 100 minutes or longer. |
| t4 | Raw eggs may be dipped, sprayed, fogged or aerosoled at temperatures equal to or above 34 degrees F. as a final treatment before packaging. Contact time with the invention's composition may be 45 minutes or longer. |
| t5 | Poultry with feathers may be dipped, sprayed, fogged or aerosoled at temperatures equal to or above 70 degrees F. as a pretreatment before de-feathering. Contact time with the invention's composition may be 15 minutes or longer. Feathers will have reduced numbers of microbes and can be dried and ready for processing. for use as fertilizer. |
| t5 | Poultry with feathers may be dipped, sprayed, fogged or aerosoled at temperatures equal to or above 70 degrees F. as a pretreatment before de-feathering. Contact time with the invention's composition may be 15 minutes or longer. Feathers will have reduced numbers of microbes and can be dried and ready for processing. |
| t6 | Poultry that has been de-feathered may be dipped, sprayed, fogged or aerosoled at temperatures equal to or above 34 degrees F. as a final treatment before packaging. Contact time with the invention's composition may be 45 minutes or longer. |

TABLE 7-continued

Exemplary Treatment Methods Used To Obtain Some Of The Data In Table 6

| Treatment Reference | Treatment Method[a] |
|---|---|
| t6 | Poultry that has been de-feathered may be dipped, sprayed, fogged or aerosoled at temperatures equal to or above 34 degrees F. Contact time with the invention's composition may be 45 minutes or longer. |
| t7 | Detached Ppoultry feathers may be dipped, sprayed, fogged or aerosoled at temperatures equal to or above 70 degrees F. as a final treatment before palletizing.further use. Contact time with the invention's composition may be 5 minutes or longer. Feathers will have reduced numbers of microbes and residual activity even after can be dried and are readydrying. for processing for use as fertilizer. |
| t7 | Detached poultry feathers may be dipped, sprayed, fogged or aerosoled at temperatures equal to or above 70 degrees F. as a final treatment before further use. Contact time with the invention's composition may be 5 minutes or longer. Feathers will have reduced numbers of microbes and residual activity even after drying. |
| t8 | Meats other than poultry, may be dipped, sprayed, fogged or aerosoled at temperatures equal to or above 34 degrees F. as a final wash. Contact time with the invention's composition may be 45 minutes or longer. |
| t9 | Meats other than poultry, maybe dipped, sprayed, fogged or aerosoled at temperatures equal to or above 34 degrees F. as a final wash. Contact time with the invention's composition may be 45 minutes or longer. The composition is preferably washedrinsed off. |
| t9 | Meats other than poultry, maybe dipped, sprayed, fogged or aerosoled at temperatures equal to or above 34 degrees F. as a final wash. Contact time with the invention's composition may be 45 minutes or longer. The composition is preferably rinsed off. |
| t10 | Hides (animal skins) may be dipped, sprayed, fogged or aerosoled at temperatures equal to or above 34 degrees F. as a pretreatment. Contact time with the invention's composition may be 5 minutes or longer. Animals may be alive or dead for this process. The composition may be left on to dry before the remainder of the processing steps. |
| t11 | Seeds and nuts may be dipped, sprayed, fogged or aerosoled at temperatures equal to or above 34 degrees F. as a final wash. Contact time with the invention's composition may be 45 minutes or longer. |
| t12 | Seeds and nuts may be dipped, sprayed, fogged or aerosoled at temperatures equal to or above 34 degrees F. as a final wash. Contact time with the invention's composition may be 15 minutes or longer. The composition is preferably washedrinsed off. |
| t12 | Seeds and nuts may be dipped, sprayed, fogged or aerosoled at temperatures equal to or above 34 degrees F. as a final wash. Contact time with the invention's composition may be 15 minutes or longer. The composition is preferably rinsed off. |
| t13 | Fish may be dipped, sprayed, fogged or aerosoled at temperatures equal to or above 34 degrees F. as a final wash. Contact time with the invention's composition may be 15 minutes or longer. |
| t14 | Shellfish may be dipped, sprayed, fogged or aerosoled at temperatures equal to or above 34 degrees F. as a final wash. Contact time with the invention's composition may be 15 minutes or longer. |
| t15 | Dried goods may be sprayed, fogged or aerosoled at temperatures equal to or above 34 degrees F. as a final wash. Contact time with the invention's composition may be Contact time with the invention's composition may be 115 minutes or longer. |
| t15 | Dried goods may be sprayed, fogged or aerosoled at temperatures equal to or above 34 degrees F. as a final wash. Contact time with the invention's composition may be 15 minutes or longer. |
| t16 | Ice may be formed with the composition that is to be used as an aid for cold storage transport and microbial reduction. The shrimp were dipped into a solution containing a bacterial inoculum, and then surrounded for 30 minutes at ambient temperature (about 62° F.) by the invention's compositions that had previously been frozen into ice cubes (about 29° F.). Materials surrounded by the ice could be rinsed off, or left without washing offrinsing to allow formation of a bio-thin, adherent film that provides continued antimicrobial activity. |
| t16 | Ice may be formed with the composition that is to be used as an aid for cold storage transport and microbial reduction. The shrimp were dipped into a solution containing a bacterial inoculum, and then surrounded for 30 minutes at ambient temperature (about 62° F.) by the invention's compositions that had previously been frozen into ice cubes (about 29° F.). Materials surrounded by the ice could be rinsed off, or left without rinsing to allow formation of a thin, adherent film that provides continued antimicrobial activity. |
| t17 | Structures may be dipped, sprayed, fogged, aerosoled, autoclaved or scrubbed in at temperatures equal to or greater than 200 degrees F. as a final wash. Contact time with the invention's composition may be 2 minutes or longer. The composition is preferably left on the surface without washing offrinsing to allow formation of a bio-thin, adherent film that provides continued antimicrobial activity |
| t17 | Structures may be dipped, sprayed, fogged, aerosoled, autoclaved or scrubbed at temperatures equal to or greater than 200 degrees F. as a final wash. Contact time with the invention's composition may be 2 minutes or longer. The composition is preferably left on the surface without rinsing to allow formation of a thin, adherent film that provides continued antimicrobial activity |
| t18 | Structures may be dipped, sprayed, fogged, aerosoled or scrubbed in at temperatures equal to or greater than 34 degrees F. as a final wash. Contact time with the invention's composition may be 10 minutes or longer. |

TABLE 7-continued

Exemplary Treatment Methods Used To Obtain Some Of The Data In Table 6

| Treatment Reference | Treatment Method[a] |
|---|---|
| t18 | Structures may be dipped, sprayed, fogged, aerosoled or scrubbed at temperatures equal to or greater than 34 degrees F. as a final wash. Contact time with the invention's composition may be 10 minutes or longer. |
| t19 | Human skin may be washed at temperatures equal to or above 34 degrees F. as an antimicrobial wash. Contact time with the invention's composition may be 2 minutes or longer. cContact time of 4-12 hours did not result in skin irritation. The moist composition may be lightly toweled off.for a dry appearance. |
| t19 | Human skin may be washed at temperatures equal to or above 34 degrees F. as an antimicrobial wash. Contact time with the invention's composition may be 2 minutes or longer. Contact time of 4-12 hours did not result in skin irritation. The moist composition may be lightly toweled for a dry appearance. |
| t20 | Human skin may be washed at temperatures equal to or above 34 degrees F. as an antimicrobial wash. Contact time with the invention's composition may be 15 minutes or longer. The composition is preferably washedrinsed off. |
| t20 | Human skin may be washed at temperatures equal to or above 34 degrees F. as an antimicrobial wash. Contact time with the invention's composition may be 15 minutes or longer. The composition is preferably rinsed off. |
| t21 | The invention's composition was circulated at temperatures equal to or above 34 degrees F. through thea RO membrane for 1 minute using a high pressure multiple centrifuge pump. |
| t21 | The invention's composition was circulated at temperatures equal to or above 34 degrees F. through a RO membrane for 1 minute using a high pressure multiple centrifuge pump. |

[a]Contact time with the invention's compositions refers to the period of time the composition is in contact with a substance before rinsing, drying, or toweling.

The above Table 6 shows the antimicrobial activity of the invention's compositions on bacterial, bacteriophage, viral, fungal and nematode microbes, using a wide variety of agricultural products (including leafy vegetables, fruiting and flowering vegetables, podded vegetables, bulb and stem vegetables, root and tuberous vegetables, Rosaceae family fruits, Bramble fruits, berries, Asian fruit, North America fruit, raw meat, raw poultry, raw seafood, fresh seeds sprouts, nuts, eggs, fresh herbs, dried herbs, spices, animal hides, feathers) and inanimate objects (such as those encountered in hospitals, food processing plants, residential buildings, office buildings, etc.).

Furthermore, the data demonstrate that, surprisingly, the invention's compositions are effective antimicrobials even at their freezing temperatures, as shown by the reduction of *E. coli* on shrimp that has been in contact with ice cubes containing the invention's compositions.

Moreover, Table 6 demonstrates the surprising differential effect of the invention's compositions on pathogenic bacteria on the one hand, and on non-pathogenic bacteria and bacteriophage on the other hand. For example, the data show higher antimicrobial activity against both the pathogenic bacteria *E. coli* (Gram-negative) and *Staphylococcus aureus* (Gram-positive) compared to the non-pathogenic *Lactobacillus* (Gram-positive) and bacteriophage T4.

Table 6 also demonstrates that the invention's compositions are suitable antimicrobials for application to human skin.

Example 3

Larger Scale Testing of Antimicrobial Activity

This example was used to demonstrate large batch processing before cutting or chopping of produce. Testing procedures were done in accordance to Example 1. Two hundred pounds of each of spinach, spring mix and iceberg lettuce were inoculated with *E. coli*. ATCC Number 43888 and the vegetables were tested using immersion and a bubbler tank The results are shown in Table 8.

TABLE 8

Antimicrobial activity (log reduction) of a combination of three components

| | *E. Coli* (ATCC 43888) inoculum 5.51-log ||||||||| 
|---|---|---|---|---|---|---|---|---|---|
| | Spinach leaf (200 pounds) ||| Spring Mix[b] (200 pounds) ||| Iceberg Lettuce (200 pounds) |||
| Component[a] | 2 min.[c] | 30 min.[c] | 180 min.[c] | 2 min.[c] | 30 min.[c] | 180 min.[c] | 2 min.[c] | 30 min.[c] | 180 min.[c] |
| (a1) Hypochlorous Acid 0.01 wgt. % & Phosphoric Acid 1 wgt. % & Propylene Glycol 2 wgt. % | 4.1 | 5 | 5.51 | 4.4 | 5.1 | 5.51 | 4.3 | 5.22 | 5.51 |

TABLE 8-continued

Antimicrobial activity (log reduction) of a combination of three components

E. Coli (ATCC 43888) inoculum 5.51-log

| Component[a] | Spinach leaf (200 pounds) | | | Spring Mix[b] (200 pounds) | | | Iceberg Lettuce (200 pounds) | | |
|---|---|---|---|---|---|---|---|---|---|
| | 2 min.[c] | 30 min.[c] | 180 min.[c] | 2 min.[c] | 30 min.[c] | 180 min.[c] | 2 min.[c] | 30 min.[c] | 180 min.[c] |
| (a2) Hydrogen Peroxide 2 wgt. % & Phosphoric Acid 1 wgt. % & Propylene Glycol 2 wgt. % | 3.5 | 4.58 | 5.51 | 3.6 | 5 | 5.51 | 3.44 | 5 | 5.51 |

[a] Components were dissolved in 350 liters of potable water and tested at about 33° F.
[b] Spring mix may contain any combination of two or more of baby lettuce, greens, endive and radicchio.
[c] The vegetables were washed in the solution containing the listed components for the period indicated.

The results demonstrate that the invention's compositions "a1" and "a2" successfully resulted in a 100% reduction of a 5.51-log *E. coli* inoculum after 180 minutes of contact in a large scale setting without altering the color, texture and/or odor of the treated produce.

Example 4

Residual Composition After Drying and/or Washing

This Example demonstrates that residual amounts of the invention's compositions remain on the treated surface, including after rinsing off, to provide continued antimicrobial activity.

TABLE 9

Residual amounts in parts per million (ppm) of component

| Component | Spinach leaf | Spring Mix | Iceberg Lettuce |
|---|---|---|---|
| Propylene Glycol | 25 | 13 | 18 |
| Phosphoric Acid | 8 | 9 | 5 |
| Hydrogen Peroxide | 0 | 0 | 0 |
| Hypochlorous Acid "CL2" | 0.001 | 0.002 | 0.001 |

Table 9 shows the results of HPLC analysis of residual amounts of components on 5 pounds of each of spinach leaf, spring mix (containing baby lettuces), and iceberg lettuce following treatment with the invention's compositions in accordance with Table 8 above, A and above. A flow through wash with 1 liter of distilled water for 60 seconds was used for HPLC residual tests.

Example 5

Applying the Compositions Pre-Harvest

Prior to harvesting fruits or vegetables, compositions (A), (B), (C) or (F) of Table 1 may be used as a pre-harvest treatment. Early in the morning or late in the evening a harvester, tractor, truck, ATV, utility vehicle or by hand could use a pre-mixed composition in a tank used for spraying, fogging, sprinkling or aerosoling. The fruit or vegetable would be covered by the composition and allowed to dry to form a film. During this drying time the antimicrobial action would continue. After the composition has dried, the edible film left after the water has evaporated, contains amounts of diol, acid and/or oxidizer that provide continued antimicrobial activity and preservative functions.

Example 6

Applying the Compositions During Harvesting

During harvesting of agricultural of the agricultural products, compositions (A), (B), (C), (D), (E), (F) or (G) of Table 1 may be used as a harvesting treatment. A harvester, tractor, truck, ATV, utility vehicle or by hand could use a pre-mixed composition in a tank used for spraying, fogging, sprinkling or aerosoling during picking procedures. If a tow behind or driven harvester is used then a dunking or immersion system may be implemented. Where the tubs, crates, bins, boxes or container with fruits or vegetables may be placed into a tank, basin or trough. This is done toto thoroughly cover the fruits or vegetables in the composition for a reasonable amount of time to ensure complete contact. After the harvesting is completed and the load of fruits or vegetables is shipped, the composition dries to form a film. During this drying time the antimicrobial activity would continue. After the composition has dried, the edible film left after the water has evaporated, contains amounts of diol, acid and/or oxidizer that provide continued antimicrobial activity and preservative functions.

Example 7

Applying the Compositions Before Washing and Bagging or Crating

When fruits or vegetables are picked or harvested, they are generally taken to a cold storage facility for chilling before they are transported for additional processing or directly to food services or stores. Before transporting, the fruits or vegetables are generally packed into plastic containers that have openings around all four sides for air circulation. The containers are easily handled by forklift or other mechanical means. As the forklift removes the containers and places them into a storage (such as cold storage) area, the forklift could carry a tank with a premixed composition of (A), (B), (C), (D), (E), (F) or (G) of Table 1 and a spray apparatus to spray the composition on the fruits or vegetables as the container is being moved. Once the container has been moved to the cooling station facility, a separate dipping or dousing station could be used to immerse the container into composition (A), (B), (C), (D), (E), (F), (G), (H) or (I) of Table k to cover the fruits or vegetables completely. The immersion tank could use a chemical handling system that utilizes a Microprocessor (analog or digital), pH electrode, Orp electrode, Dissolved Oxygen electrode, Free Chlorine electrode or DPD system. The system would use a signal representing the available composition to turn on chemical pumps, valves or auger to add additional chemicals and or water to make compositions for use in the tank.

After the container has been immersed it would be removed to drain and dry. During this drying time the antimicrobial activity would continue. After the composition has dried, the edible film left after the water has evaporated, contains amounts of diol, acid and/or oxidizer that provide continued antimicrobial activity and preservative functions.

Example 8

Applying the Compositions During Washing and Bagging or Crating

Once the fruits or vegetables have been brought into the washing and packaging facility they are typically conveyed either by a belt, flume or motorized table. During this transit the fruits or vegetables are washed with either aqueous sprays or aqueous submersion. The composition (A), (B), (C), (D), (E), (F), (G), (H) or (I) of Table 1 may be part of the aqueous solution used to clean the fruits or vegetables. This solution may also contain various oxidizers, defoamers, surfactants, oils, pesticides, dirt, and or bugs. The composition could either mix into the added makeup water or the recycled water. In either case the composition could be inserted as combined ingredients or as independent ingredients. The composition, either combined or independent, could be pump fed or gravity fed into a suction side of a pump, tank inlet, vessel inlet, trough inlet, flume inlet that is used for recycle or makeup water, or into the main supply line for the sprays or for the transport submersion. A microprocessor, analog or digital, pH electrode, Orp electrode, Dissolved Oxygen electrode, Free Chlorine electrode or DPD system may be used for automatic control. The system would use a signal representing the available composition to turn on chemical pumps, valves or auger to add additional chemicals. Alternatively, a pre-mixture of the composition could be added based on time, flow, level, turbidity, bio-load, microbial load, etc.

After the fruits or vegetables have been washed they are usually rinsed off. The composition could be in the rinse water. After the fruits or vegetables are rinsed they are usually dried, then metered to a packaging station. Alternately, prior to the packaging station, the composition could be sprayed, fogged or aerosoled, and the composition is allowed to dry into a very thin film. The edible film left after the water has evaporated contains amounts of diol, acid and/or oxidizer to provide continued antimicrobial activity and preservative functions.

Example 9

Shelf Life of Oxidizer

This Example was carried out to determine the stability of the exemplary oxidizer hypochlorous acid in the presence and absence of diol and at different pH. The level of hypochlorous acid was determined using a standard DPD assay.

TABLE 10

Hypochlorous acid stability and shelf life

| | Chlorine (ppm) | |
| --- | --- | --- |
| Minutes | Composition "x1a"[a] | Chlorine Solution[b] |
| 1 | 50 | 50 |
| 15 | 50 | 50 |
| 20 | 50 | |
| 30 | 40 | 50 |
| 45 | 38 | |
| 60 | 35 | 50 |
| 80 | 33 | |
| 90 | 27 | 50 |
| 100 | 25 | |
| 115 | 22 | |
| 125 | 20 | |
| 135 | 18 | |
| 150 | 13 | |
| 170 | 10 | |
| 190 | 7 | 50 |
| 220 | 3 | |
| 240 | 0 | |
| 400 | | 50 |
| 800 | | 50 |
| 1600 | | 48 |
| 2000 | | 45 |
| 2300 | | 43 |
| 2700 | | 41 |
| 3000 | | 40 |
| 3500 | | 38 |
| 4300 | | 36 |

[a]Composition "x1a" is referred to in Table 2, and contains ortho-Phosphoric acid 0.03 wgt. %, propylene glycol 0.02 wgt. %, hypochlorous acid 0.005 wgt. % at pH 4 (FIG. 1A).
[b]"Chlorine solution" contains ortho-phosphoric acid 0.001 wgt. % and hypochlorous acid 0.005 wgt. % at pH 7 (FIG. 1B).

The data in Table 10 and FIG. 1 show that hypochlorous acid in solution was less stable in the presence of diol at pH 4, reaching 0% at about 4 hours, compared to 100% in the absence of diol at pH 7.

Each and every publication and patent mentioned in the above specification is herein incorporated by reference in its entirety for all purposes. Various modifications and variations of the described methods and system of the invention will be apparent to those skilled in the art without departing from the scope and spirit of the invention. Although the invention has been described in connection with specific embodiments, the invention as claimed should not be unduly limited to such specific embodiments. Indeed, various modifications of the described modes for carrying out the invention which are obvious to those skilled in the art and in fields related thereto are intended to be within the scope of the following claims.

I claim:

1. An aqueous composition comprising
 a) from 0.001 wgt. % to 2 wgt. % phosphoric acid,
 b) from 0.01 wgt. % to 1 wgt. % propylene glycol, and
 c) from 0.01 wgt. % to 5 wgt. % chlorine,
wherein said composition (i) has acidic pH and (ii) has antimicrobial activity.

2. The composition of claim 1, wherein the amount of said phosphoric acid alone and said propylene glycol alone has lower antimicrobial activity compared to antimicrobial activity of a combination of said phosphoric acid and said propylene glycol.

3. The composition of claim 1, wherein said composition further comprises an additional oxidizing agent.

4. The composition of claim 3, wherein said additional oxidizing agent comprises an unstabilized oxidizing agent.

5. The composition of claim 3, wherein said composition comprises from 0.001 wgt. % to 30 wgt. % of said additional oxidizing agent.

6. The composition of claim 1, wherein said composition further comprises a surfactant.

7. The composition of claim 6, wherein said composition comprises from 0.001 wgt. % to 0.1 wgt. % surfactant.

8. The composition of claim 1, wherein said composition comprises from 0.01 wgt. % to 0.10 wgt. % phosphoric acid.

9. The composition of claim 1, wherein said composition comprises from 0.09 wgt. % to 0.15 wgt. % propylene glycol.

10. The composition of claim 1, wherein said composition comprises from 0.01 wgt. % to 1 wgt. % chlorine.

11. The composition of claim 1, wherein said composition is at a temperature from below said composition's freezing temperature to 120° C.

12. The composition of claim 1, wherein antimicrobial activity of (a) said phosphoric acid, (b) said propylene glycol, (c) said chlorine, (d) a combination of said phosphoric acid and of said propylene glycol, (e) a combination of said phosphoric acid and of said chlorine, and (f) a combination of said propylene glycol and of said chlorine, is lower than antimicrobial activity of a combination of said phosphoric acid, of said propylene glycol and of said chlorine.

13. An agricultural product having a surface film that comprises the aqueous composition of claim 1.

14. An agricultural product comprising a contacted surface that is produced by a method comprising
   a) providing
      i) a first surface comprising a first number of microbes, and
      ii) an antimicrobially effective amount of a composition selected from the group consisting of the composition of claim 1 and the composition of claim 4, and
   b) contacting said first surface with said composition under conditions that produce a contacted surface comprising a reduced number of said microbes compared to said first number of said microbes on said first surface in the absence of said contacting.

15. A method for reducing discoloration of an agricultural product, comprising
   a) providing
      i) an agricultural product having a first surface,
      ii) an anti-discoloration effective amount of the composition of claim 1, and
   b) contacting said agricultural product with said composition under conditions that produce a contacted surface having reduced discoloration compared to discoloration of said first surface in the absence of said contacting.

16. The method of claim 14, wherein said contacting is at a temperature from 30° F. to 40° F.

17. The method of claim 16, wherein said contacted surface comprises a 100% reduced number of said microbes compared to said first number of said microbes on said first surface in the absence of said contacting.

18. The method of claim 14, wherein said agricultural product comprises one or more of fruit, vegetable, herb, seed, nut, meat, poultry, seafood, and poultry egg.

19. A method for making an aqueous antimicrobial composition that contains the composition of claim 1, comprising
   a) providing
      i) phosphoric acid,
      ii) propylene glycol, and
      iii) unstabilized chlorine,
   b) mixing said phosphoric acid and said propylene glycol in water to produce a first mixture, and
   c) mixing said chlorine with said first mixture to produce an aqueous antimicrobial composition that contains the composition of claim 1.

20. The method of claim 19, further comprising mixing a surfactant in said aqueous antimicrobial composition.

21. An aqueous antimicrobial composition produced by the method of claim 20.

22. A method for reducing the number of microbes on a surface, comprising
   a) providing
      i) a first surface comprising a first number of microbes, and
      ii) an antimicrobially effective amount of the composition of claim 1, and
   b) contacting said first surface with said composition under conditions that produce a contacted surface comprising a reduced number of said microbes compared to said first number of said microbes on said first surface in the absence of said contacting.

23. The method of claim 22, wherein said first surface comprises a pathogenic microbe and a non-pathogenic microbe, and said reduced number of said microbes comprises a greater reduction in the number of said pathogenic microbes than in the number of said non-pathogenic microbes.

24. The method of claim 22, wherein said method further comprises c) drying said contacted surface to produce a dried surface comprising one or more of said acid and of said propylene glycol.

25. The method of claim 22, wherein said method further comprises c) washing said contacted surface under conditions that reduce the amount of one or more of said acid and of said propylene glycol on said contacted surface.

26. The method of claim 22, wherein said composition has a temperature from below said composition's freezing temperature to 120° C.

* * * * *